United States Patent
Kamins

(10) Patent No.: US 8,348,811 B2
(45) Date of Patent: Jan. 8, 2013

(54) ORTHOPEDIC THERAPY SYSTEM AND DEVICE AND A METHOD OF USE

(76) Inventor: Paul Kamins, Lancaster, PA (US)

( * ) Notice: Subject to any disclaimer, the term of this patent is extended or adjusted under 35 U.S.C. 154(b) by 0 days.

(21) Appl. No.: 12/193,659

(22) Filed: Aug. 18, 2008

(65) Prior Publication Data

US 2009/0048074 A1 Feb. 19, 2009

Related U.S. Application Data

(63) Continuation-in-part of application No. 11/840,712, filed on Aug. 17, 2007, now abandoned.

(51) Int. Cl.
*A63B 22/06* (2006.01)
(52) U.S. Cl. .................. 482/52; 482/57; 482/9
(58) Field of Classification Search ............. 482/51–52, 482/57–65, 1–9; 601/5, 24, 32, 36
See application file for complete search history.

(56) References Cited

U.S. PATENT DOCUMENTS

| | | | | |
|---|---|---|---|---|
| 2,747,300 A * | 5/1956 | Field | | 36/7.5 |
| 3,058,120 A * | 10/1962 | Smith et al. | | 623/28 |
| 3,738,649 A * | 6/1973 | Miller | | 482/57 |
| 3,902,199 A * | 9/1975 | Emmert | | 623/28 |
| 3,968,963 A * | 7/1976 | Sileo | | 482/57 |
| 4,069,893 A * | 1/1978 | Blackstone | | 182/200 |
| 4,255,822 A * | 3/1981 | Dixon | | 623/28 |
| 4,570,926 A * | 2/1986 | Ensmenger | | 482/75 |
| 4,648,593 A * | 3/1987 | Wilkinson | | 482/52 |
| 4,659,075 A * | 4/1987 | Wilkinson | | 482/52 |
| 4,700,946 A * | 10/1987 | Breunig | | 482/57 |
| 4,805,901 A * | 2/1989 | Kulick | | 482/63 |
| 4,838,547 A * | 6/1989 | Sterling | | 482/128 |
| 4,912,638 A * | 3/1990 | Pratt, Jr. | | 600/595 |
| 4,993,407 A * | 2/1991 | Chen | | 601/36 |
| 5,011,139 A * | 4/1991 | Towley, III | | 482/38 |
| 5,033,736 A * | 7/1991 | Hirschfeld | | 601/36 |
| 5,035,418 A * | 7/1991 | Harabayashi | | 482/62 |
| 5,080,353 A * | 1/1992 | Tench | | 482/130 |
| 5,112,296 A | 5/1992 | Beard et al. | | |
| D326,695 S * | 6/1992 | Evans | | D21/670 |
| 5,118,101 A * | 6/1992 | Belli | | 482/52 |
| 5,160,305 A * | 11/1992 | Lin | | 482/138 |
| 5,312,313 A * | 5/1994 | Holmes et al. | | 482/95 |
| 5,472,396 A * | 12/1995 | Brazaitis | | 482/57 |
| 5,492,515 A * | 2/1996 | Charnitski | | 482/51 |
| 5,499,959 A * | 3/1996 | Holmes et al. | | 482/95 |
| 5,536,225 A * | 7/1996 | Neuberg et al. | | 482/71 |
| 5,540,639 A * | 7/1996 | Potts et al. | | 482/95 |
| 5,551,529 A * | 9/1996 | Molitor | | 182/204 |
| 5,554,083 A * | 9/1996 | Chen | | 482/95 |
| 5,569,128 A * | 10/1996 | Dalebout | | 482/57 |
| 5,601,515 A * | 2/1997 | Matsumoto | | 482/57 |
| 5,647,822 A * | 7/1997 | Avganim | | 482/60 |
| 5,672,141 A * | 9/1997 | Johnston | | 482/57 |
| 5,679,100 A * | 10/1997 | Charnitski | | 482/51 |

(Continued)

*Primary Examiner* — Stephen Crow
(74) *Attorney, Agent, or Firm* — Perry E. Van Over and Associates PLLC

(57) ABSTRACT

Provided is a novel physical therapy system and device that can be manually operated by a post-operative patient without the need of professional on site assistance, wherein the degree of movement of the limb or joint of interest is measured and recorded so as to provide a record of the progress of the prescribed post-operative therapy for immediate feedback to the patient as well as for long term data recordation for the therapist or physician.

8 Claims, 16 Drawing Sheets

U.S. PATENT DOCUMENTS

| | | | |
|---|---|---|---|
| 5,709,636 A | 1/1998 | Vallone et al. | |
| 5,722,420 A * | 3/1998 | Lee | 600/546 |
| 5,782,639 A * | 7/1998 | Beal | 434/29 |
| 5,853,005 A | 12/1998 | Scanlon et al. | |
| 6,087,934 A | 7/2000 | Golab | |
| 6,159,201 A | 12/2000 | Hamilton et al. | |
| 6,238,320 B1 | 5/2001 | Flanagan | |
| 6,368,260 B1 * | 4/2002 | Crews | 482/142 |
| 6,419,613 B2 * | 7/2002 | Stearns et al. | 482/57 |
| 6,517,586 B2 * | 2/2003 | Lin | 623/28 |
| 6,652,425 B1 * | 11/2003 | Martin et al. | 482/57 |
| D485,369 S * | 1/2004 | Ranagan et al. | D25/68 |
| 6,692,411 B1 * | 2/2004 | Stearns et al. | 482/57 |
| 6,730,003 B1 * | 5/2004 | Phillips | 482/57 |
| 6,799,660 B1 * | 10/2004 | Crawford | 182/200 |
| 6,821,234 B1 * | 11/2004 | Barbee | 482/57 |
| 6,918,860 B1 * | 7/2005 | Nusbaum | 482/57 |
| 6,932,745 B1 * | 8/2005 | Ellis | 482/52 |
| 6,979,284 B2 * | 12/2005 | Curtis | 482/57 |
| 7,520,840 B2 * | 4/2009 | Shifferaw | 482/52 |
| 7,662,070 B1 * | 2/2010 | Mann | 482/57 |
| 7,703,845 B2 * | 4/2010 | Smith et al. | 297/195.11 |
| 2002/0061804 A1 * | 5/2002 | Hasegawa | 482/57 |
| 2002/0077221 A1 * | 6/2002 | Dalebout et al. | 482/57 |
| 2002/0077704 A1 * | 6/2002 | Lin | 623/28 |
| 2002/0082147 A1 * | 6/2002 | Wu | 482/57 |
| 2003/0203793 A1 * | 10/2003 | Emmert | 482/75 |
| 2004/0092368 A1 * | 5/2004 | Gramaccioni | 482/70 |
| 2005/0085346 A1 * | 4/2005 | Johnson | 482/57 |
| 2005/0101887 A1 | 5/2005 | Stark et al. | |
| 2005/0202940 A1 * | 9/2005 | Simmons | 482/75 |
| 2005/0255971 A1 | 11/2005 | Solomon | |
| 2005/0277517 A1 * | 12/2005 | Snyderman | 482/52 |
| 2006/0035772 A1 | 2/2006 | Golesh et al. | |
| 2006/0122039 A1 * | 6/2006 | Lee et al. | 482/57 |
| 2006/0191745 A1 * | 8/2006 | McAllister | 182/121 |
| 2006/0235544 A1 | 10/2006 | Iversen et al. | |
| 2007/0110017 A1 | 5/2007 | Fulknier et al. | |
| 2007/0167296 A1 * | 7/2007 | Hika | 482/76 |
| 2008/0220946 A1 * | 9/2008 | Chang | 482/57 |

* cited by examiner

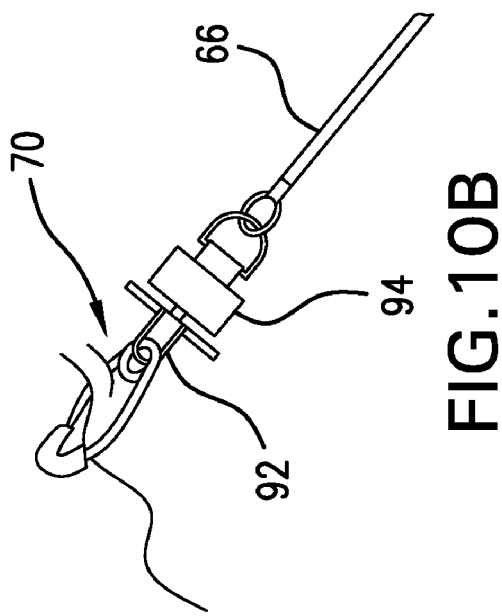
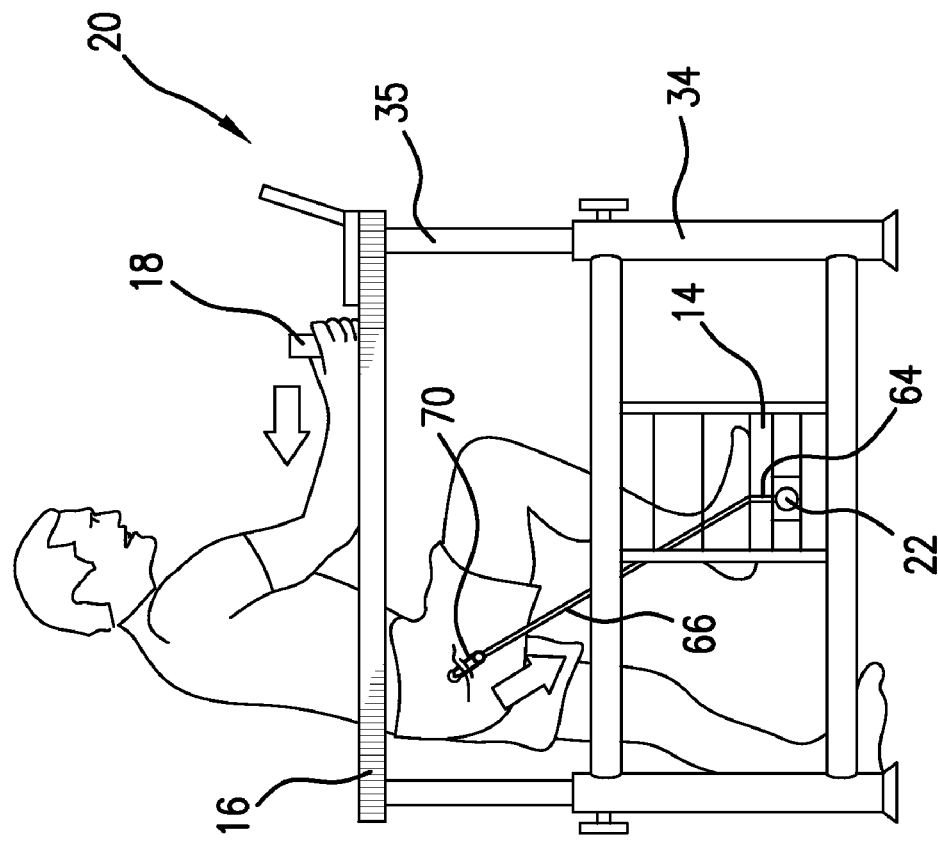

ORTHOPEDIC THERAPY SYSTEM AND DEVICE AND A METHOD OF USE

BACKGROUND OF THE INVENTION

1. Technical Field

The present invention relates to orthopedic therapy and in particular to devices that provide dynamic measurable therapy for use by orthopedic patients. More particularly, the present invention relates to a physical therapy system and device that can be manually operated by a post-operative patient without the need of professional on site assistance, wherein the degree of movement of the limb or joint of interest is measured and recorded so as to provide a record of the progress of the prescribed post-operative therapy for immediate feedback to the patient as well as for long term data recordation for the therapist or physician.

2. Background Art

The success of joint reconstructive or replacement surgery depends largely upon the postoperative rehabilitation process. This is particularly true for a total knee arthroplasty. In total knee arthroplasty surgeons are typically able to achieve a great, range of joint motion for the sedated patient on the operating table. However, the quantity and quality of the post-operative therapy is critical to the patient's ultimate range of motion and therefore, the ultimate success of the surgical procedure. A limited range of motion of a post-operative joint, particularly a knee, will result in pain and limited function. It is generally understood that there is a six-week window of opportunity after surgery during which a patient can, through therapy and exercise, maximize his ultimate range of motion for the post-operative joint. Very important to the success of any post-operative therapy is the patient's commitment to maximizing the effort to rehabilitate the affected joint. Conventional post-operative therapies necessarily have to enlist the patient's commitment to and compliance with the prescribed regime as much as possible. However, the success of the postoperative therapy in large part relies more on the therapist contribution than on passive mechanized therapy devices that may or may not be properly, routinely, and adequately employed by the patient.

Continuous passive motion (CPM) machines and/or manually applied physical therapy to an injured or post operative limb are the primary rehabilitation treatments chosen by most doctors and therapists. Many limb and joint exercising devices are known. Generally, these machines have a motor driven limb support with the limb support capable of being set to periodically move the limb in a preset range of positions for a preset length of time and at a preset speed. Once these parameters have been selected the machine automatically moves the limb from a straightened position back and forth to these pre-selected positions at the pre-selected speeds and durations.

One major drawback to these motor driven machines is the problem of selecting the optimum settings for the machine. While resetting positions and safety cut-off switches are usually provided for the user, the initial settings for the machines, which are set by the therapist, are frequently too severe and painful. Later, as the therapy progresses and the joint becomes more limber and capable of greater movement the settings are often insufficient and therefore less helpful in taking the rehabilitation as far as possible.

Further, conventional therapy machines and therapists cannot sense the level of pain experienced by the patient during movement of the joint or the true degree of stiffness of the joint. For this reason, the rehabilitative therapy provided to the patient may be too severe or too reserve. Only the patient is truly aware of what joint motion limits he is capable of reaching on any given day of the rehabilitative period.

A conventional rehabilitative therapy regime for a post-operative total knee replacement would include both the use of a therapist and a continuous passive motion (CPM) machine. In use, the patient would lie down and securely strap his knee into the machine. The machine with its preset motion, speed, and duration parameters would be turned on while the patient passively endured the machine bending the knee to a prescribed range of motion. The range of motion can be adjusted by the therapist to a level he believes to be within the patient's pain and motion tolerance; however the level of uncertainty of the optimum settings for any given patient is high. The CPM is typically prescribed for self-use at home by the patient for a period of several weeks after surgery. During this rehabilitative period the involvement of a physical therapist in providing manipulative therapy and in monitoring the use of the CPM is generally considered the most important element in a successful rehabilitation regime. Even if the settings on the CPM are relatively appropriate for the patient, it remains that the effectiveness of the CPM in the rehabilitative regime is totally dependent upon the amount of effective use it receives. The physical therapist working with the postoperative patient can improve the rehabilitation progress by monitoring the patient's use of the CPM and by passively stretching the patient's knee and recording the progress; however this spot-checking of the patient's use of the CPM is at best periodic and isolated and not necessarily a true picture of whether or not the patient is making good use of the machine. Further, inconvenience, forgetfulness, pain avoidance and many other reasons can contribute to the patient's neglect of his prescribed CPM and home therapy regime. For this reason, the therapist's sessions with the patient are often the most effective part of the rehabilitative effort. Unfortunately, the patient's sessions with the therapist will, at best, be limited to about 45 minutes for each of two or three sessions per week for six weeks. Over the six week long post-operative period the therapist will likely spend no more than 13 to 15 hours working with the patient. For this reason, a good therapist will typically prescribe a variety of additional exercises to assist the patient in the effort of stretching the knee into flexion and extension during those long periods when the patient is at home without the benefit of the therapist presence. For example, extension of the knee joint is often augmented by having the patient prop an object under his heel after which the patient will press the knee downward from above. Flexion exercises are more difficult. Efforts to improve flexion of the knee can be augmented by the patient sitting on a chair and pulling the operative leg back with the opposite leg. While these and other self-help exercises can be useful, they are only beneficial if the patient exercises a great deal of self-discipline and strictly adheres to the prescribed program. The patient is typically left alone to exercise or to neglect his prescribed therapy program for the majority of those initial few weeks when a therapy program can be most effective. Further, although the time during which the therapist is actively involved in sessions with the patient is of great value, it remains that providing such professional assistance is becoming increasingly expensive for the patient and his insurance company. Limited finances or insurance can curtail or abruptly end the active assistance of a professional therapist. For this reason, it is very important that, within reasonable cost constraints, the best possible tools be provided to aid the patient in the self-administered portion of the exercise program.

Another important aspect of the patient's rehabilitation program is the requirement to accurately measure and report the degree of flexion and extension of the joint in a timely manner. It is very important that the therapist and the surgeon are aware of the progress being made by the patient in order to permit course corrections in the therapy program as needed. At present, the degree of flexion or extension of a joint is measured by the therapist using a goniometer, an angle finder, which the therapist holds on the side of the patient's knee and uses his best-guess to align the device with the leg. The therapist generally uses this conventional angle measurement technique intermittently to determine the level of progress in the rehabilitative effort being made by the patient. Studies presented at the Orthopedic Trauma Association (OTA) 2000 meeting indicated that a visual inspection and angle estimation of a joint by an attending surgeon, an orthopedic fellow, and an orthopedic senior resident varied from the actual angle of the joint as determined by radiological examination by an average of 6.5° and the difference between the goniometer measurement and the radiologically determined angle was only slightly better at 5.6°. In addition, a significant difference in 1 of 8 comparisons among attending surgeons, fellows and residents was found (Poster No. 82, OTA 2000 Posters). Further, the inaccuracy of visual or goniometer estimates of a joint angle can also be attributable to the obvious possibility that the therapists estimate of proper alignment of the goniometer to the patient's leg can vary considerably from one visit to the next; what seems like progress from an earlier session may only be the result of inaccurate instrument alignment at a subsequent session. This is particularly true when a substitute therapist must attend to the patient. In such cases an inconsistent alignment of the goniometer should be expected and therefore the recorded progress would be expected to be erroneous.

To date there has been no therapy system provided that effectively enables the patient to completely control all parameters of his rehabilitative machine exercise therapy so as to actively stretch the knee joint with immediate biofeedback as well as precise recordation of therapy progress. Further, the accuracy of any recordation of the level of progress using conventional measurement techniques and devices is at best questionable. What is needed is a joint rehabilitative therapy system that allows the patient alone to conveniently use the device on a daily basis wherein the parameters of the degree of extension and flexion, speed, and duration are established by the patient using a real time biofeedback mechanism and allowing the patient to limit or extend the effort to conform to his pain threshold rather to that which a therapist has applied a best-guess.

SUMMARY OF THE DISCLOSURE

It is a primary object of the present invention to meet the above identified need by providing a novel exercise therapy system for rehabilitation of a post-operative joint that can be manually operated by the patient, the system being capable of providing both immediate biofeedback to the patient and recordation of the therapy progress.

It is another object of the invention to provide a system for rehabilitative exercise therapy that is convenient and safe to be used under the manual control of the patient such that the patient, being fully aware of the pain level and joint movement limitations, can maximize the benefit of the therapy in a controlled, measured manner with the benefit of immediate biofeedback on the degree of extension and flexion of the affected joint.

It is another object of the invention to provide a system for rehabilitative exercise therapy that the patient can easily adjust to increase the therapeutic benefit, without the need of professional assistance, as the course of rehabilitative therapy progresses.

It is another object of the present invention to provide a system for rehabilitative exercise therapy that can be ergonomically configured to provide a stable platform to maximize biomechanical leverage for exercise therapy that is controlled and adjusted by the patient using information provided by the immediate biofeedback of degree of joint extension and flexion achieved.

It is another object of the invention to provide a system for joint rehabilitation exercise therapy that records the progress of the therapy for study by the surgeon or therapist.

It is another object of the invention to provide a system for joint rehabilitation that is operated by the patient alone, the system including a remote data link capable of transmitting printable information on the progress of the therapy to a surgeon or therapist supervising the therapy progress.

It is another object of the invention to provide a system for joint rehabilitation that includes an exercise platform having mechanisms with servo-assist that are capable of ergonomically reconfiguring the platform as needed.

Also provided is a novel system for joint rehabilitation therapy that can be provided as a kit to be easily assembled and operated by a patient without the need for professional assistance.

Also provided is a method for performing effective joint rehabilitation therapy using the system of the present invention.

BRIEF DESCRIPTION OF THE DRAWINGS

The foregoing and other features of the disclosed device will become apparent to one skilled in the art to which the present invention relates upon consideration of the following description of exemplary embodiments with reference to the accompanying drawings, wherein:

FIGS. 10A-b respectively show (FIG. A) a side view of the novel therapy system with an exemplary device frame with a depiction of a patient physically positioned on the exercise platform with the cable clip of the linear cable encoder properly positioned adjacent to the patient's hip joint and attached to the patient's outer garment; (FIG. B) a close-up view of the cable clip showing the preferred embodiment of a pin, which can be attached to the patient's clothing and securing a two-part quick disconnect with an attached cable of a linear cable encoder.

DETAILED DESCRIPTION OF PREFERRED EMBODIMENTS

Detailed embodiments of the present invention are disclosed herein and represented in FIGS. 1-11; however, it is understood that the following description and each of the accompanying figures are provided as being exemplary of the invention, which may be embodied in various forms without departing from the scope of the claimed invention. Thus, the specific structural and functional details provided in the following description are non-limiting, but serve merely as a basis for the invention as defined by the claims provided herewith. The system described below can be modified as needed to conform to further development and improvement of materials without departing from the inventor's concept of the invention as claimed.

The concept of the invention is to provide a system that can be used by a patient for exercise therapy for any part of the body requiring post-operative or post-injury physical rehabilitation. The following non-limiting description is directed to the invention configured for use by a patient requiring therapy for the knee joint; although the same principles of the invention can be adapted to provide exercise therapy for other joints such as, for example, shoulder, elbow, wrist, hip, ankle, and hand.

The present invention, in contrast to the conventional continuous passive machine (CPM), which uses a motorized mechanism to move the affected joint of the patient, can be viewed as a continuous active machine (CAM), in which the patient takes an active role in moving the affected joint as well as in controlling the steady progress of the therapy regime, The present invention enables the patient to continually use the system on a daily basis as compared to conventional therapy programs, which include only isolated visits with the therapist.

It is of great advantage that the present invention is a system that can include interchangeable attachments that facilitate maximal flexion, maximal extension, and continuous fluid motion exercise therapy. It is also an advantage that the system can be shipped disassembled to a patient's home and then assembled for use in a convenient, frequently accessed area where the patient without any professional assistance can use the invention throughout the day to achieve a continuing active therapy regime that provides immediate feedback to the patient on the level of progress achieved. Unlike the conventional CPM device, the present invention allows the patient to monitor the progress of the therapy and conveniently take an active roll in the daily progress of the therapy. The real time feedback of improvement or lack thereof in the angle or range of joint articulation by the patient enables the patient to immediately identify his daily progress, challenge himself, and adjust his exercise regime to maximize the benefit of the system.

Figure 3:
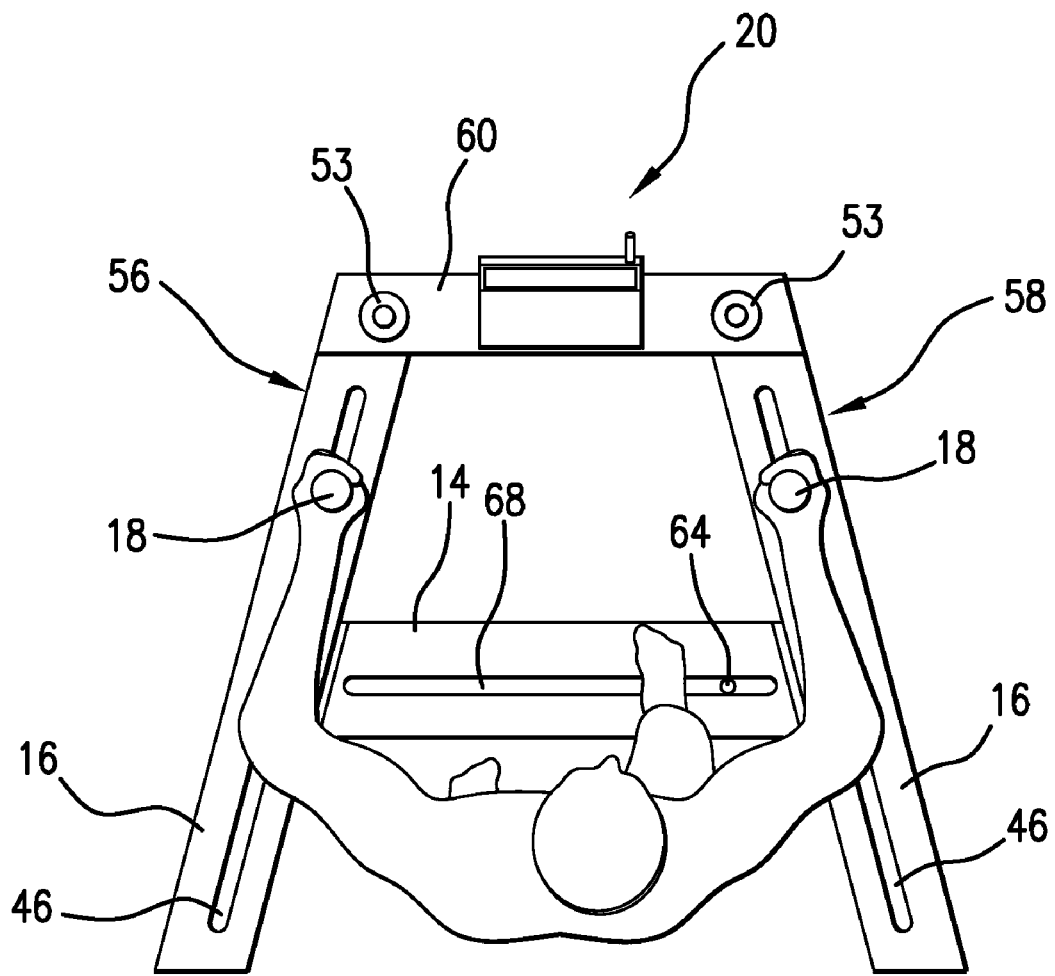
FIG. 3 shows a top view of the novel therapy system with an ergonomically configured sidewall taper.

The exemplary orthopedic therapy system described herein and generally shown in the accompanying figures at 10 includes an exercise platform assembly, generally shown at 12 that can be adjusted for a particular patient's anatomical proportions as needed. The platform assembly 12 can be ergonomically conformed to different aspects of the patient's body as needed; for example, the patient's height, upper arm length, and forearm reach. The platform assembly includes an exercise step 14, which can be easily adjusted by the patient to greater or lower elevations relative to the platform 12 as needed during the course of the prescribed exercise regime. Such ergonomic adjustments can provide the maximum biomechanical advantage during the exercise session as well as provide the user with a sense of greater stability and security. For patients who are recovering from an injury and may be inclined to avoid exercise out of concern for falling and re-injuring themselves, the ergonomically adjustable platform with adjustable forearm rests 16 and adjustable hand grips 18 can be of great benefit in providing a level of safety and confidence that will promote the frequent and regular use of the system 10. Further, the platform assembly 12 can be provided with an ergonomic taper of the sidewalls, the left side and right side assemblies 56, 58. As shown in FIG. 3, this taper opens the platform assembly and allows the patient's shoulders to rotate laterally (to unlock) as the patient causes his upper body to lower between the sidewalls. Advantageously, this results in increased biomechanical pressure on the knee during flexion.

Also included in the system 10 is a biofeedback assembly, generally shown at 20, that can provide real time biofeedback to the patient during the course of the exercise session. The biofeedback assembly 20 can be useful to the progress of the therapy by providing instantaneous feedback such that the user is aware of his level of success in bending or straightening the post-operative knee and being made so aware can, within self-imposed stiffness and pain limitations, increase his effort to maximize the benefit of each therapy session. Further, the biofeedback assembly 20 can be programmed to include a standardized or personalized ideal course of progress for flexion and extension of the joint so as to provide a running goal for personal achievement by which the patient can measure his daily progress. The embodiment of the biofeedback assembly 20 described herein and shown in the figures is exemplary of the concept of the biofeedback assembly 20, which is only limited by the claims attached hereto. The exemplary biofeedback assembly 20 can include a data collection device exemplified herein as a linear cable encoder 22 in combination with a computing device 24, a data display device 26, and a parameter data input terminal 28. The biofeedback assembly 20 can also include a data transmission device 30 having components, which can be a separate and distinct component or can be at least partially contained within the housing of any of the other components of the biofeedback assembly 20. The system 10 can be battery powered and/or be solely dependent upon connection to an external power source through the power input 32.

Figure 1:
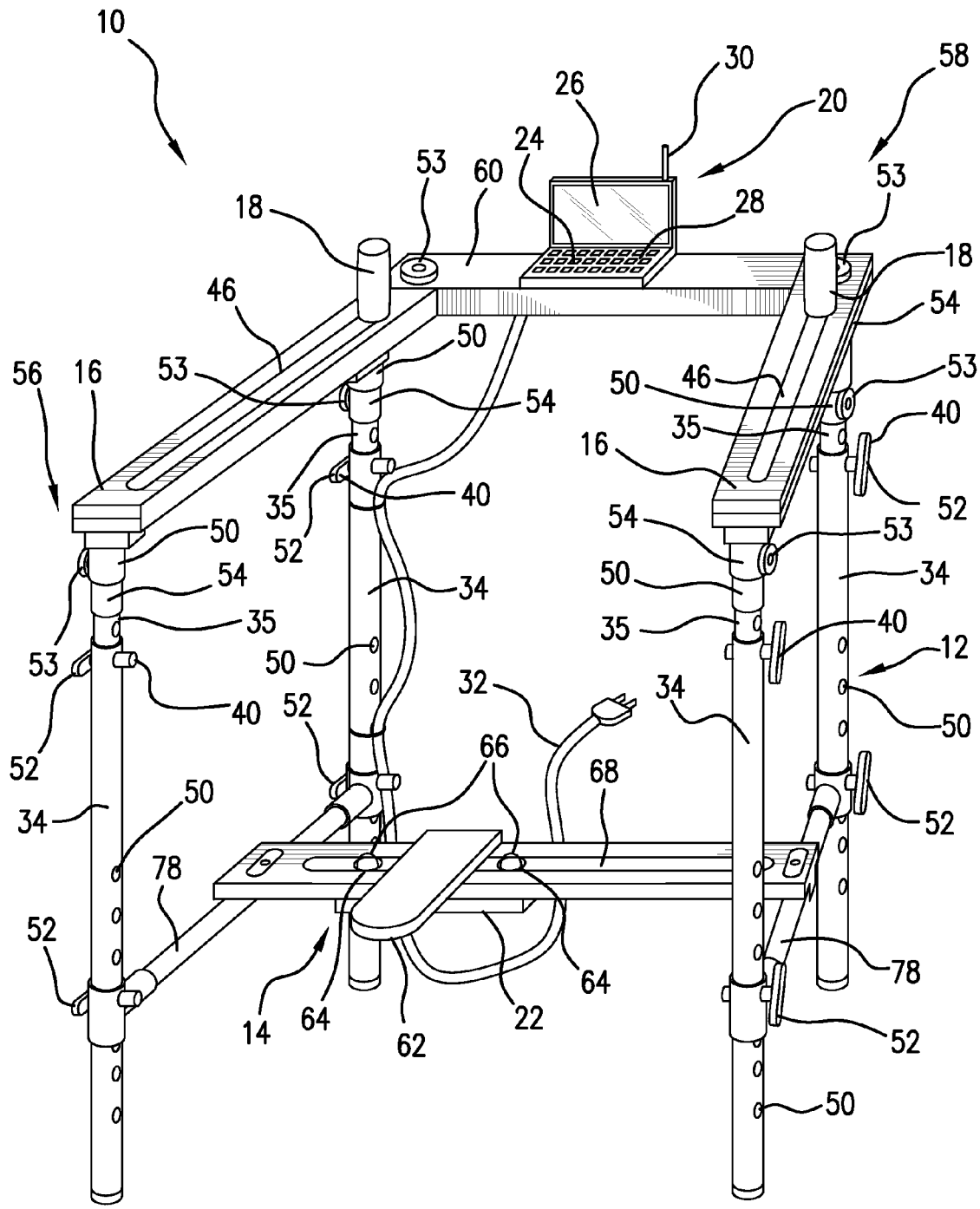
FIG. 1 shows an isometric view of the novel therapy system including the ergonomically adjustable device frame for supporting the patient during the exercise regime, the biofeedback assembly, and the data recordation assembly.
Figure 2:
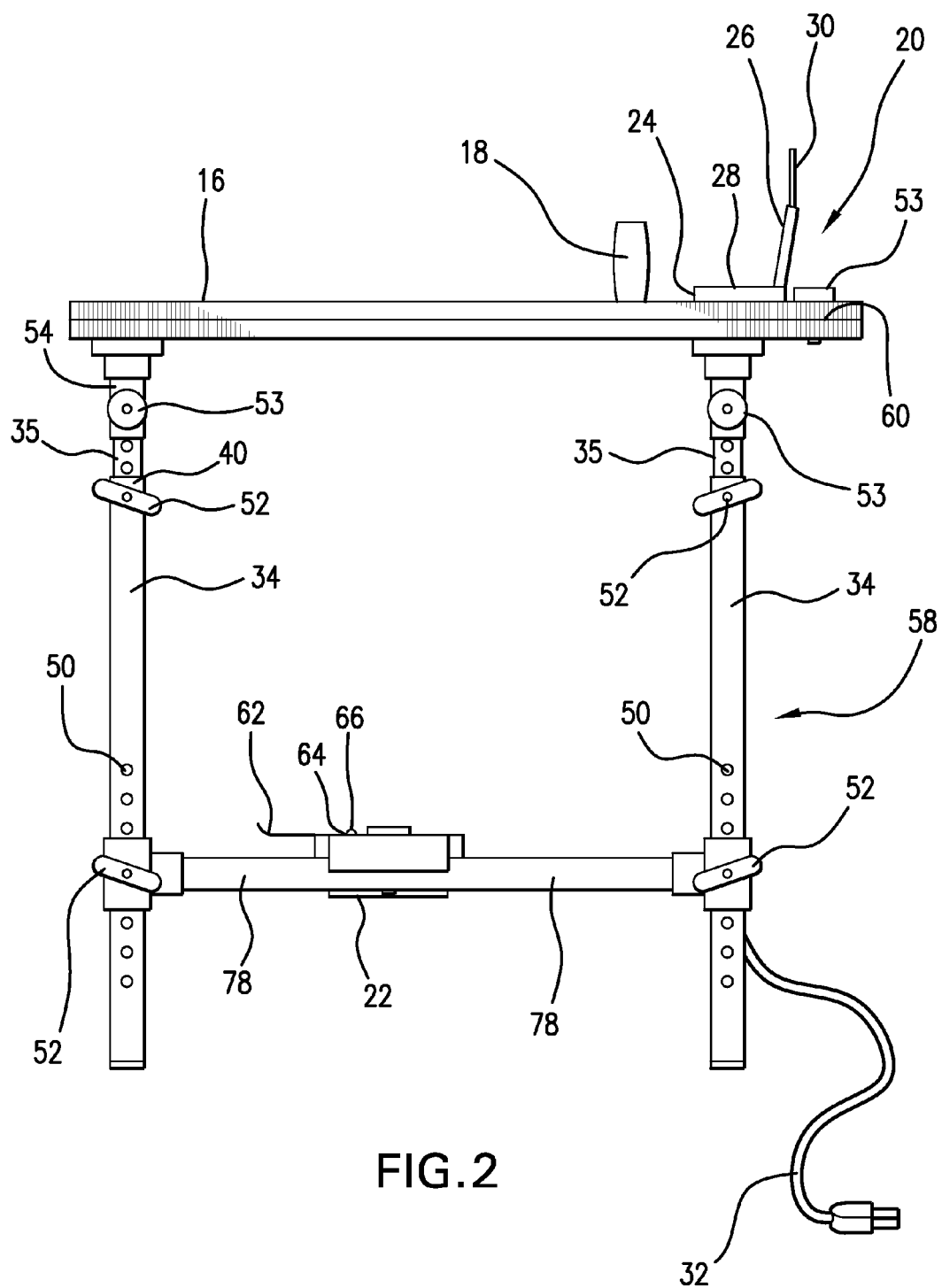
FIG. 2 shows a side view of the novel therapy system with an exemplary device frame.
Figure 9:
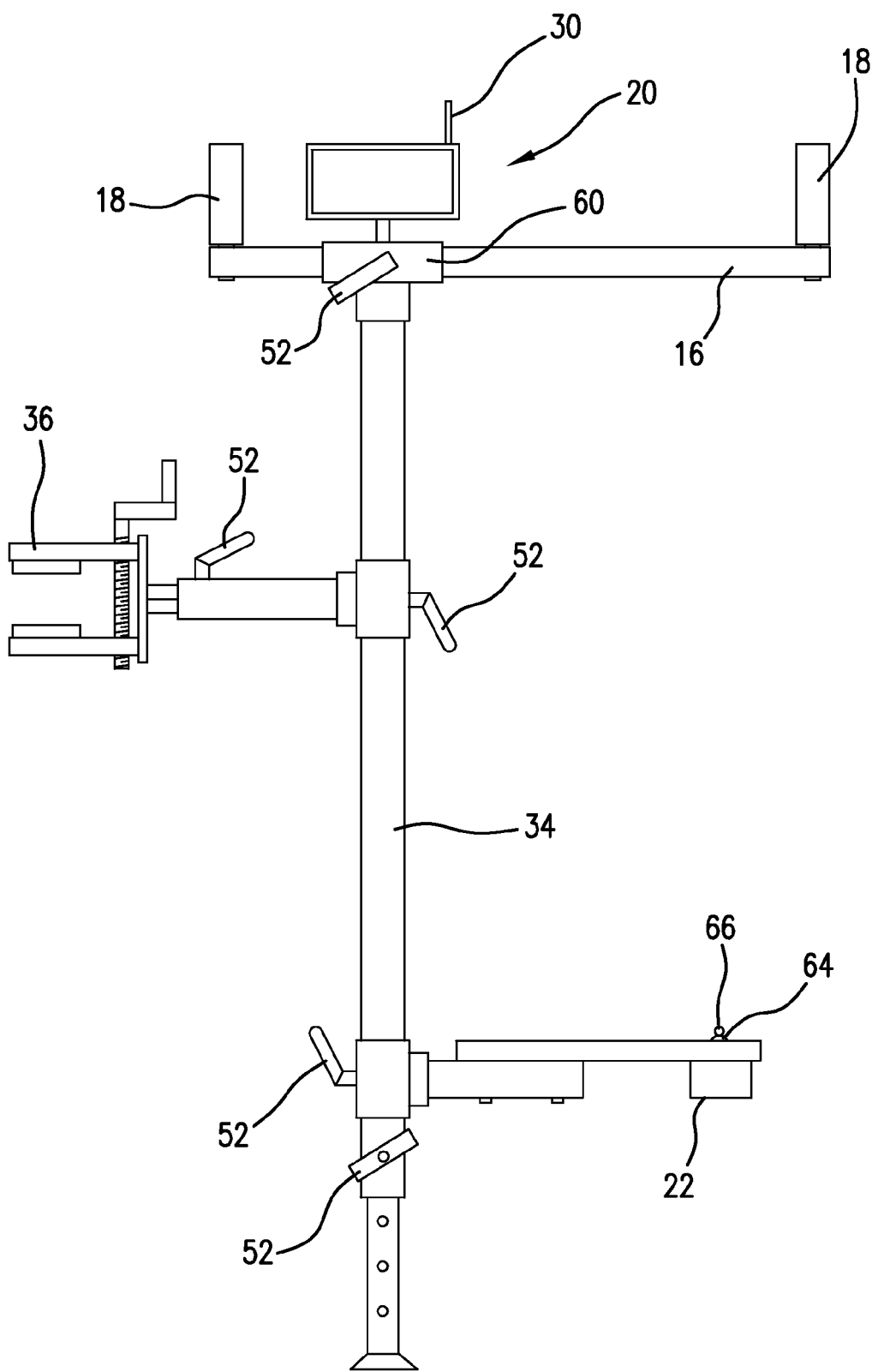
FIG. 9 shows an isometric view of the novel therapy system including an alternative single upright support embodiment of the platform assembly.
Figure 11:
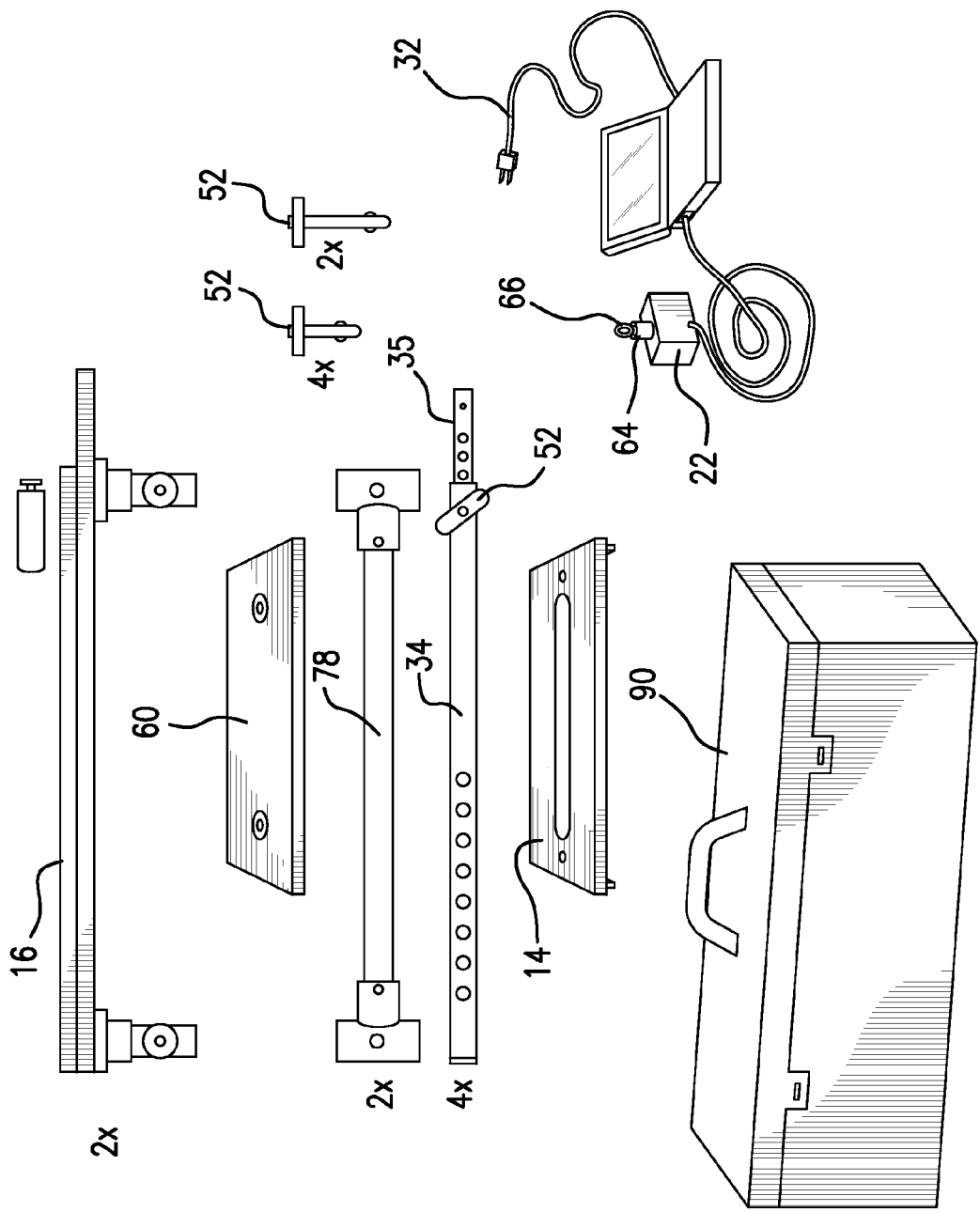
FIG. 11 shows some representative components of the novel therapy system and a transport container for the same that can be provided as part of a kit. The device so provided can be easily assembled and disassembled for return shipment in the container to the provider.

As best shown in FIGS. 1-2 the platform assembly 12 can include at least one upright support 34. It is preferred that the platform assembly 12 include four upright supports; however, it is within the concept of the invention to provide an alternative, but still stable, platform assembly that can have as few as one upright support, as shown in FIG. 9. Providing stability for an embodiment of the present invention that includes less than four upright supports, such as a tripod, a bipod, or a single upright support, might require that the platform assembly be securely connected to a table or counter top, or some other stabilizing structure by a security bracket 36. Preferably, the security bracket 36 can be configured to universally attach to a wide variety of stabilizing structures and be so attached with an easily operated locking and unlocking connection mechanism 38.

The at least one upright support 34, can be preferably provided with a length adjustment mechanism 40 as a means to enable the patient to easily adjust the height of the platform assembly 12 to be ergonomically configured to the patients' body height. Preferably, coordinated adjustment of the upright support length adjustment mechanism 40 for each of the upright supports 34 can be done so as to bring the forearm rests 16, which serve as upper attachments for at least two upright supports 34, to a level that is suitably comfortable for the patient. While any known mechanism for providing an upright support length adjustment feature for the device can be used within the concept of the invention, as shown in FIGS. 1, 2, 4, 5A, and 9, a preferred easily operated length adjustment mechanism 40 can include the well known concept of providing upright support members 34 having internally disposed, extendable telescoping members 35 with a locking mechanism, which can include through holes in the upper portion of the telescoping member 35 and position locking pins, such as for example, quick release ball lock pins 52 sized for easy passage through the locking holes 50. The ball pins 52 conventionally have a push button lock release and are commercially available through companies such as Fairlane Products, Inc.™. While such ball pins are a preferred element of the length adjustment mechanism 40, it is within the concept of the present invention to employ any releasable locking device, such as cotter pins and the like to facilitate the operation of the length adjustment mechanism 40. As best shown in FIG. 1, a left or right pair of upright supports 34 are connected one to the other at their respective tops by the forearm rest 16 and also connected one to the other at a lower position along the shaft of the upright supports by a step support member 78. This additional lower positioned step support member 78 provides a support connection for the exercise step 14 and also provides greater stability to the entire platform assembly.

An additional ergonomic adjustment feature of the present invention that can be provided is an adjustable position hand grip mechanism 42, as shown in FIGS. 1, 2, 3, 4, 5A, and 8. A preferred embodiment of adjustable hand grip mechanism 42, includes two opposing hand grips 18, having hand grip guide members 44 respectively positioned to easily slide within hand grip adjustment slots 46, which are defined along the longitudinal axis and through the body of the forearm rests 16, and hand grip releasable locking retainers 48. Prior to beginning an exercise session, the patient can easily slide the hand grips 18 along the pathway defined by the adjustment slots 46 to a point that is perceived by the patient to be ergonomically suitable. The locking retainers 48 can then be secured so as to hold the hand grips 18 in the selected position for the exercise session. As needed, the patient can easily release the locking retainers 48 and adjust the position of the hand grips 18.

As best shown in FIGS. 1, 2, 4, and 5A, the stability of the platform assembly is derived from the secure connection of the upright supports 34 to the forearm rests 16. Similar to the exemplary telescoping upright length adjustment mechanism 40, this connection of the upright supports 34 to the forearm rests 16 can be easily and securely accomplished by connection of the telescoping members 35 to arm rest connection elements 54 using securing pins, which preferably can be quick release ball lock pins 52, which are sized for easy passage through the locking holes 50 and the armrest connection elements 54. While any other known connection means, such as cotter pins, nut and bolt, screw, and the like can be employed to connect the forearm rests 16 and the upright supports 34, this preferred embodiment provides a secure means of connection that can be easily assembled or disassembled as needed.

Figure 4:
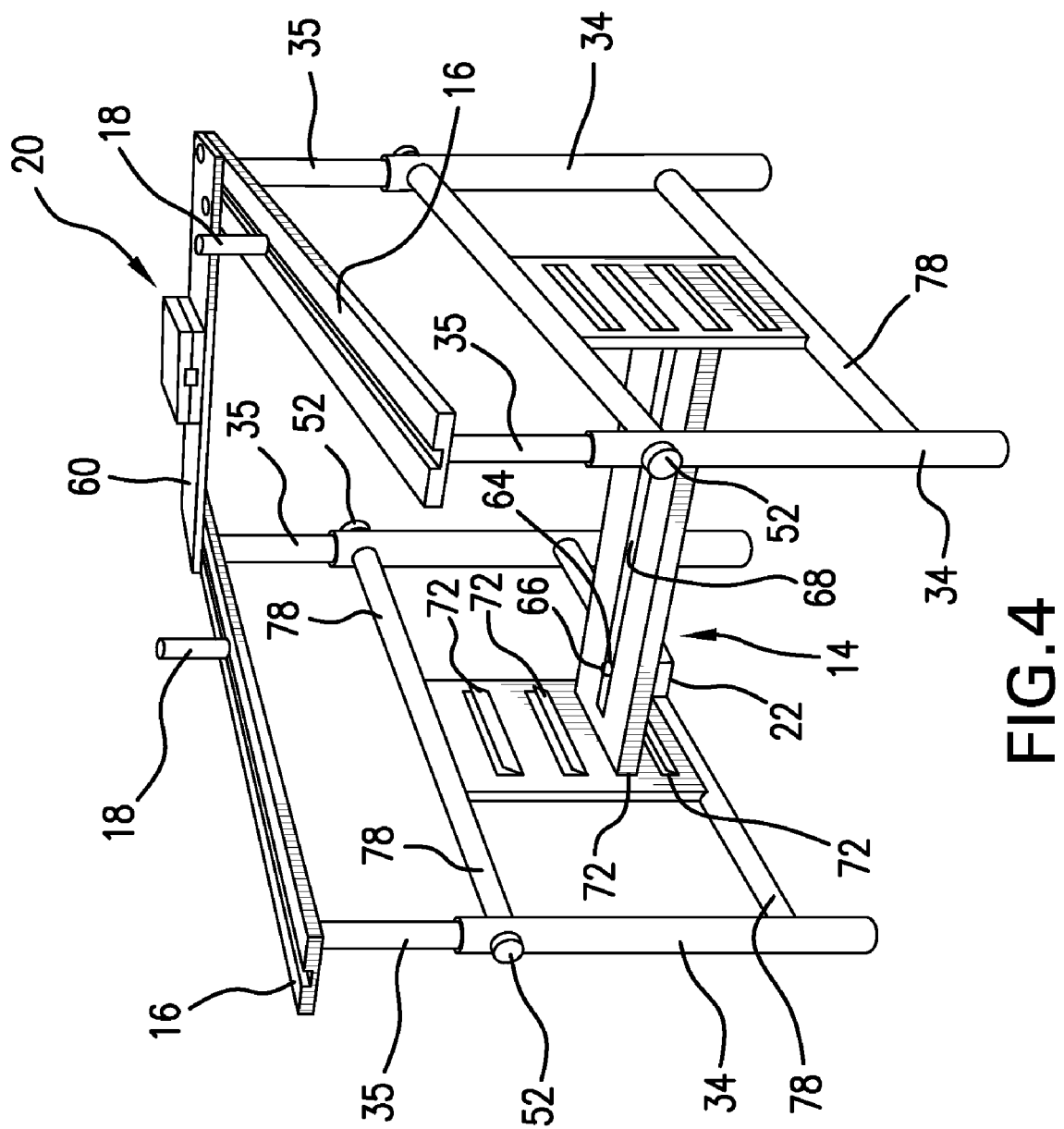
FIG. 4 shows an isometric view of the novel therapy system including another example of the platform assembly with an alternative step adjustment mechanism.
Figure 5A:
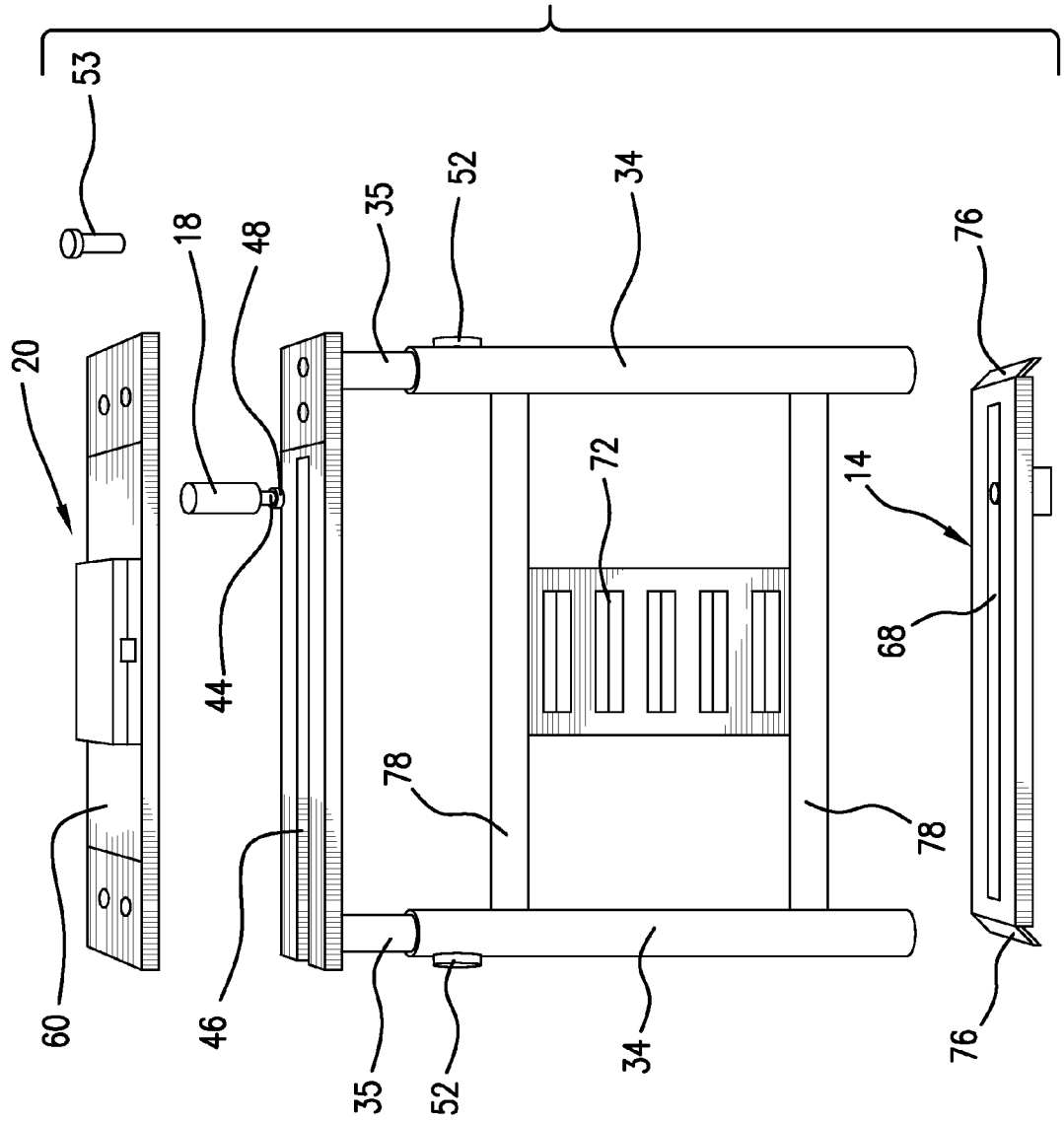
FIGS. 5A-5B respectively show some components of the device frame of FIG. 4 and a detail of the alternative step adjustment mechanism and method of step adjustment.
Figure 5B:
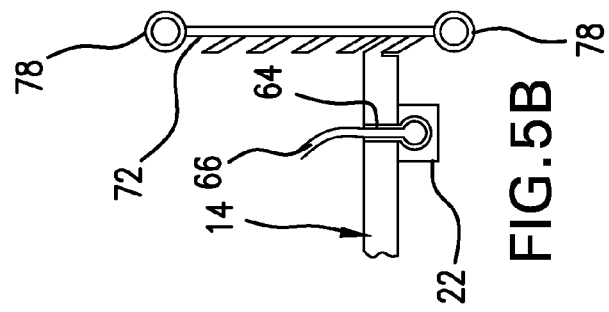

As best shown in FIGS. 1 and 4, in the preferred embodiment, a left side assembly, generally shown at 56, is assembled by the combination of the two upright supports 34 that are connected by the forearm rest 16 that would normally be provided for the patient's left forearm. Similarly, the two upright supports 34 connected to the forearm rest normally provided for the patient's right forearm, when assembled, form a right side assembly, generally shown at 58. A console connection member 60 can be provided, as shown in FIGS. 1, 3, 4, 5A, and 8, to connect the left side assembly 56 to the right side assembly 58. To maximize the strength and stability of the connection of the console connection member 60 to the left and right side assemblies 56, 58, it is preferred that a secure assembly connector 53 be employed such as, for example a threaded bolt engaging a threaded hole defined in the platform or alternatively engaging a threaded nut. For ease of assembly and disassembly of the exercise platform 12, the threaded bolt can be provided with a hand tightened grip such as a fluted knob. Although the strength of such a threaded connection for the console connection member 60 to the upright supports 34 via the interposed telescoping members 35 is preferred, it is within the concept of the invention to provide any known connector for that purpose such as, for example, through holes provided in the components and quick release locking pins 52, cotter pins, or the like.

A final component of the system which is essential to the success of a progressive exercise regime and also adds stability to the platform assembly 12 is the exercise step 14. As shown in FIGS. 1 and 2, the level of the exercise step can be elevated by a simple adjustment of the position of the step 14 using the locking pins 52. While the step 14 does provide greater stability for the platform assembly 12 as a lower connection point between the left side assembly 56 and the right side assembly 58, its primary value to the system is in providing a weight bearing step upon which the patient can place his foot and, as he can bear, press his body weight on to the step and thus exercise the post-operative knee joint. By adjusting the height of the step 14, the patient can lower his upper body weight on to the post-operative knee in a controlled fashion. As the patient progresses in his therapy over time, he can raise the step thereby allowing greater force of body weight in flexing his post-operative or post-injury knee joint. At the lowest step, which appropriately would be used in the earlier part of the rehabilitation program, a mild force would be applied as would be suitable for the pain and discomfort in a recent post-operative knee. As the step is raised to higher levels, the force placed on the post-operative knee would increase. Importantly, the patient using this system can, as his joint stiffness and pain threshold permits, adjust the level of the step to suit his needs without having to rely solely on the judgment of external observations by a therapist.

FIGS. 4 and 5 show an alternative mechanism for height adjustment of the step 14. In this alternative embodiment, the height of the step can be adjusted by simply moving the step 14 out of the lateral support grooves 72 located on the step support panel 74, relocating the step 14 to another level, and placing the step back into a secure position. Lateral step supports 76, which are complimentary to the lateral support grooves 72, can be provided on the outer edges of the step 14.

The step 14 can be provided with a foot placement locator 62, which can be a distinct heel locator or guide as shown in FIGS. 1, 2, and 9, or can be simply a position on the step 14 that is adjacent to the location of the linear cable encoder 22. In either case, the foot is properly positioned adjacent to the at least one cable outlet 64 of the linear cable encoder 22. As shown in FIG. 1, the linear cable encoder 22 can be provided with a cable outlet 64 located on each side of the foot placement locator 62. Preferably, a single cable outlet 64, as shown in FIG. 4 can be provided. Importantly, whichever embodiment of the invention is employed, it is important that prior to use the cable outlet 64 be positioned so as to allow extension of the cable 66 on the lateral side of the foot so as to permit extension of the cable upward along the lateral surface of the leg to a point adjacent to the hip joint of the patient. The greater trochanter of the femur is a reproducible prominence on the side of the hip joint, which can be easily located by tactile means. The cable, once extended can be attached to the outer clothing of the patient at a reproducible position over the location of the greater trochanter using any fastener that is suitable to provide a secure releasable attachment. Any variety of pins, clips, hook and loop fasteners, and the like can be used without departing from the spirit of the invention. As shown in FIGS. 10A-B, a preferred method of easily and consistently making the attachment of the cable 66 to the correct anatomical position adjacent the patient's greater trochanter is to provide a separate fastener or cable clip 70 that is configured for easy connection and disconnection to the end of the cable 66. A preferred embodiment is to provide the cable clip 70 as a two-part quick disconnect device as is known in the art. However, this separate clip can be as simple as a safety pin connected to a cable attachment ring, so long as the clip can be easily attached to the outer garment of the patient and when using the device, the patient can easily attach the end of the cable 66 to the clip. As shown in FIGS. 1, 3, 4, 5A, and 8, the linear cable encoder can be slidably positioned to any position selected by the patient along the longitudinal axis of the step 14. The cable outlet 64, in the preferred embodiment extends from the linear cable encoder 22 located beneath the exercise step 14 through guide slot 68 defined along the longitudinal axis of the body of the step 14. In addition to providing the exit portal for the tensioned, coiled cable 66 from the encoder 22, the cable outlet 64 also serves as a guide pin for this sliding movement of the linear cable encoder 22 as the cable outlet 64 travels along the guide slot 68. By this adjustable position feature of the linear cable encoder 22, the patient can selectively position the encoder 22 to a location on the step 14 that is suitable for a therapy program for the left knee or for the right knee as necessary.

In practice, during the initial assembly of the system the patient can adjust the length of the upright supports 34 as well as the position of the hand grips 18 to suit his anatomical needs. Such adjustments can be facilitated by pre-marked settings on the upright supports 34 and the forearm rests 16. He positions the step 14 to the proper height adjustment using the preferred adjustment mechanism or the alternative step adjustment mechanism displayed in FIGS. 4 and 5. He can then adjust the position of the linear cable encoder to conform to the left knee or right knee therapy regime as prescribed. The patient then fastens the cable 66 via the cable clip 70 to his outer garment at a position on the lateral side of his leg adjacent to the greater trochanter. As earlier discussed and as best shown in FIG. 10B, this attachment of the cable 66 to the outer garment of the patient is preferably accomplished using a two-part quick disconnect device as the cable clip 70. The patient can attach the upper portion 92 of a quick disconnect clip to the garment and then subsequently attach the cable 66 via the lower portion 94 of the quick disconnect clip at any time throughout the day as the patient desires to use the device 10. When the patient places his foot on the step 14 he is ready to commence the exercise session.

Figure 6:
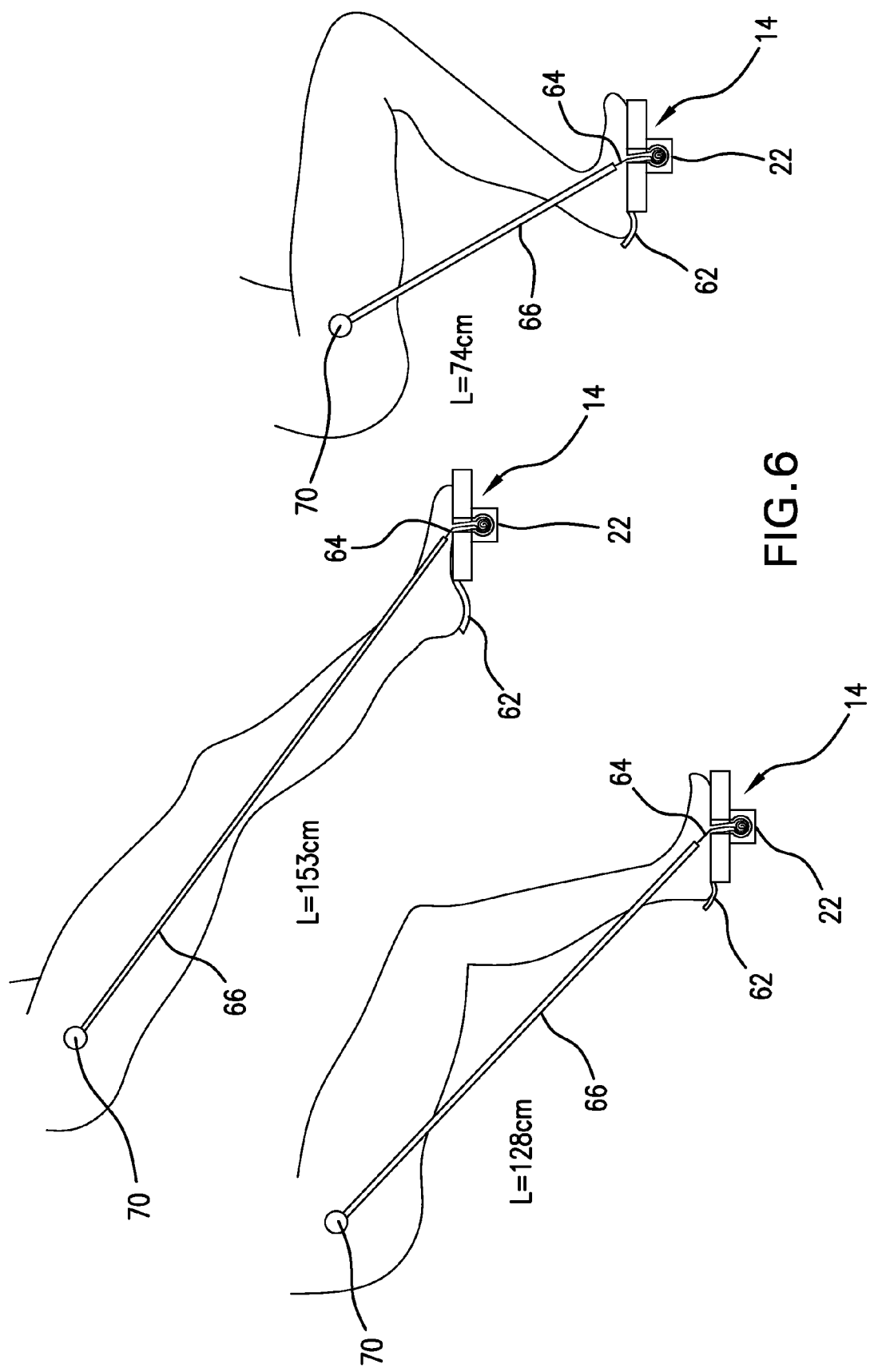
FIG. 6 shows depictions of a patient's leg in flexion, extension, and partial extension positions with the distal end of a cable extending under coiled tension from a linear cable encoder properly positioned and attached on the lateral aspect of the patient's leg (to the outer garment in practice) during use of the system. Exemplary comparative measurements of the cable length for each of the three positions are annotated on the figure.
Figure 7:
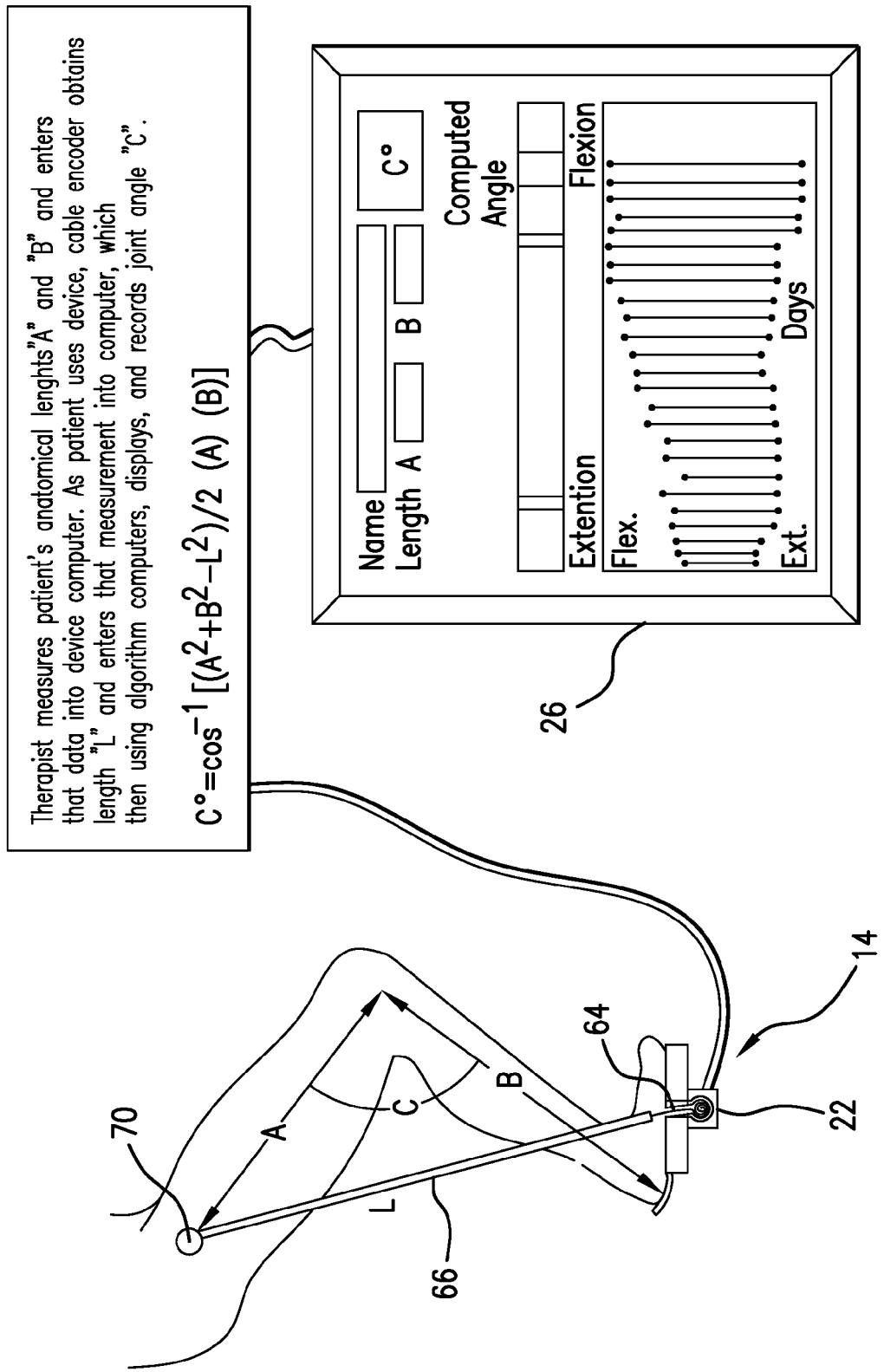
FIG. 7 shows a diagram of an exemplary joint angle measurement mechanism including a depiction of a the lateral aspect of a patient's leg with a tension coiled cable extending from a linear cable encoder properly attached (to the outer garment in practice) and an exemplary display showing the upper leg and lower leg measured preset lengths of "A" and "B" respectively, the measured distance of "L" as determined by the length of the cable of a linear cable encoder, the programmed algorithm of the linear cable encoder computing device, and an exemplary display of the present parameters, measured cable length, computed angle "C" of the joint at issue, and a display of real time computations of flexion and extension as well as a display of flexion and extension progress over time as can be recorded in the computing device of the encoder.

The linear cable encoder 22 of the device 10, in its simplest form, can be provided with a simple counter, which provides a record of the sum of repetitions of the extension and retraction of the cable 66 from the cable encoder 22. As earlier discussed and as shown in FIGS. 6 and 7, it is preferred that the linear cable encoder 22 record the length "L" of the extension of the cable 66 and provide a computation of the angle of the knee during extension and flexion. Prior to beginning exercise repetitions on the device 10 having the preferred embodiment of the cable encoder 22, the patient can note the number on the display for "L" (length of the cable extended by the linear cable encoder) as a comfortable resting position with his foot on the step. An example of a comfortable resting position is '128 mm as shown in FIG. 6. Also shown are exemplary measurements of "L" for extension and flexion. The patient's goal is to make the distance as small as possible while working on flexion of the joint. This is accomplished by lowering his buttocks downward toward his ankle. The cable extends from the cable outlet 64 up to the hip as the patient puts his weight on the step and raises his buttocks up and away from his ankle. The absolute number recorded for "L" is unimportant; it is only important that the patient makes progress in decreasing the number measured as he further flexes his knee. Similarly, in extension, the patient's goal is to increase the number of the measurement for "L"; that is increasing the distance from the buttocks to the ankle. By consistency in positioning of the foot on the step 14 and attachment of the cable clip 70 on the patient's outer garment, the measurement reading obtained by the linear cable encoder 22 will provide a very accurate assessment of the patient's progress. As shown in FIG. 6, the actual measurement of "L" is from the cable outlet 64 of the cable encoder 22, not from the patient's ankle; however, this slight difference in length is not sufficient to be of significance to the computations provided by the biofeedback assembly 20 and further are of no relevance to the goal of the device 10 of providing immediate information of the patient's progress in achieving improved flexion and extension of the knee.

As shown in FIG. 6, the differences in length "L" of the extended cable 66 from the linear cable encoder can vary considerably depending upon the degree of flexion or extension of the knee. The patient's awareness of the differences in these measurements of "L" alone can provide sufficient biofeedback to allow the patient to determine the progression of his therapy program. However, as earlier indicated, and as shown in FIG. 7, the biofeedback assembly 20 of the system 10 in addition to the data collection device exemplified as a linear cable encoder 22 with a simple counter can include a computing device 24, a data display device, a data input terminal, and a data transmission device. The computing device can be programmed with an algorithm for determining the number of degrees in a selected angle of a triangle when the lengths of the three sides of the triangle are known, That algorithm, $C.°=\cos^{-1}[(A^2+B^2-L^2)/2\ (A)\ (B)]$, as shown in FIG. 7, when programmed into the biofeedback assembly 20 of the system 10 will convert the entered measurement data of the anatomical lengths of the upper leg (A) the lower leg (B), and the measured length "L" of the cable of the linear cable encoder 22 into a computed angle (C.°) of extension or flexion of the knee. This "angle measurement," as universally referred to by surgeons and therapists can be displayed immediately to the patient during the course of the exercise session. Such real time biofeedback has never before been possible. In addition to this immediate biofeedback to the patient, the data can be saved for later evaluation by the patient's surgeon or therapist. It is also within the concept of the invention that the data, before or after analysis, be transmitted by cable, satellite, or wireless means to the office of the surgeon and/or therapist to provide a more immediate report on the progress of the patient's prescribed therapy. The frequency of this data link reporting can be programmed for download or transmission on call when the system is prompted by a remote telephonic or computer link prompt from the a requesting party such as the surgeon or therapist or it can be programmed for data transmission at specific times during the prescribed therapy program.

Alternatively, other distance measuring or range finding systems can be employed to determine the degree of movement of a patient's limbs when using the device. Other preferred measurement systems could be used such as, for example, a laser emitter/receiver system attached to the step 14 in place of the most preferred linear cable encoder 22 can be employed to measure the distance from the step 14 to a laser reflector attached to the patient's outer garment adjacent to the hip joint at the position of the greater trochanter without departing from the concept of the invention herein disclosed.

In addition to the benefits of the system discussed above, the platform assembly 12 can be useful for other exercises that are beneficial as the rehabilitation process proceeds. For example, if the patient moves the handle grips 18 back along the forearm rests 16, they can be used as a stabilizing force for exercises of the hip. Toe raises can also be performed using this configuration of the platform assembly 12. Further, if the patient moves the hand grips 18 to their most forward position on the forearm rests 16 and then he steps up onto the step 14 and then down again while maintaining his hold on the hand grips 18, the platform 12 can be employed as a stair stepper to increase quadriceps strength.

Figure 8:
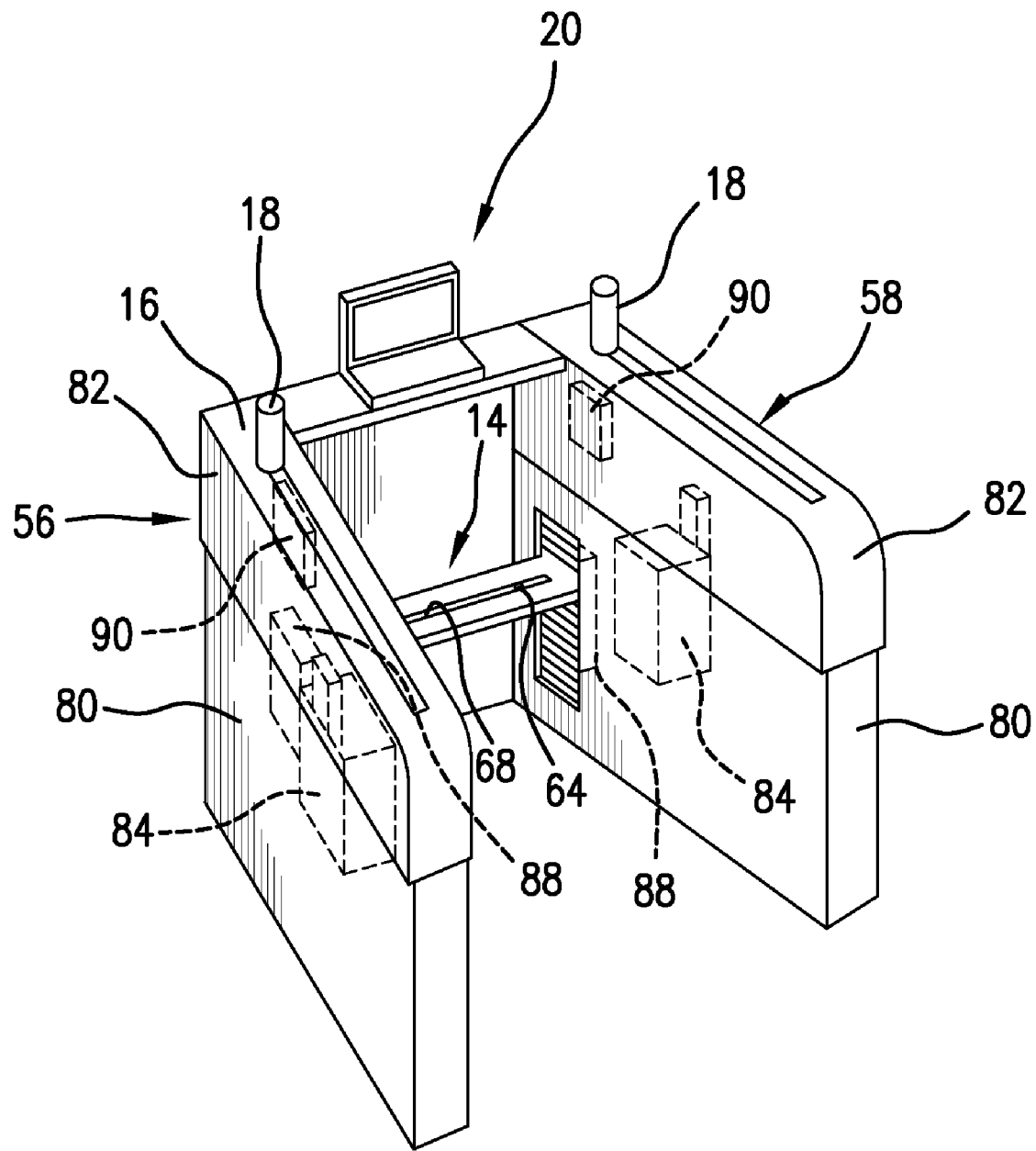
FIG. 8 shows an isometric view of the novel therapy system including an alternative embodiment of the platform assembly. The exemplary alternative platform assembly can be of uni-body construction and can have servo-assisted upward telescoping left and right side assemblies as well as servo-assisted step and handle position adjustments. The system can also be equipped with a variety of alternative biofeedback assemblies and be suitably employed in a high use environment such as a therapy department or the office of a therapist.

In addition to the exemplary alternative embodiments of the platform assembly 12, which are shown in FIGS. 3, 4, 5A, and 9, the system can be provided with a uni-body component construction platform assembly, such as shown in FIG. 8. In such an embodiment, the strength of the platform can be derived from the entirety of the uni-body construction rather than from the sum of the strength provided by the pipe components of the platform, as shown in FIG. 1. The height adjustment feature for this alternative uni-body construction embodiment can be provided by telescoping left and right side assemblies 56, 58 having a lower portion 80 and an upper portion 82. The upper portion 82 can be slidably displaced upward or downward relative to the lower portion 80 as a means of adjusting the height of the alternative uni-body platform. Servo-assist motors with height position adjustment mechanisms 84, as are well known in the art, can be provided internal to the uni-body construction and are therefore not openly shown in FIG. 8. Additionally, handle servos and adjustment mechanisms 86 and step servos and adjustment mechanisms 88 can be provided to facilitate ergonomic adjustment of these components. This uni-body construction embodiment of the present invention is well suited for a more stationary environment such as the a physical therapy department or a physical therapists office and as such can be equipped with alternative biofeedback systems such as, for example, the well known electromagnetic tracking device known in the art as "Flock of Birds." Other alternative biofeedback devices can also be employed such as, for example, laser emitter/receiver devices, visual spatial orientation devices, radio-tracking devices, or any other advanced means of determining the angle "C" of a skeletal joint.

The preferred tubular or pipe component construction, as shown in FIGS. 1, 2, 3, 4, 5A-B, 9, 10A, and 11, requires considerable structural strength in each component such as can be provided by aluminum, steel, titanium, or alloys thereof. However, it is within the concept of the present invention that the exercise platform 12 can also be fabricated by wood, high density polymers, light weight composites or any other material having sufficient strength to provide a structurally safe platform assembly 12 for the device 10.

As described above and partially shown in FIG. 5A, the system 10 can be provided as a fully or partially disassembled kit. The kit can be shipped in a container 90 and easily assembled by the patient without need of professional assistance.

The above description of the embodiment of the invention configured with an adjustable step to facilitate maximal flexion exercise therapy, as described above, describes the basic components and theory of use of the novel exercise system. A more preferred embodiment of the invention, described below, can include interchangeable attachments to facilitate maximal flexion, maximal extension, and continuous fluid motion exercise therapy in a single ergonomically adjustable platform. The more preferred embodiment having multiple interchangeable attachments is described in FIGS. 12-16 and includes an exercise platform assembly, generally shown at 12a that can be adjusted for a particular patient's anatomical proportions as needed. As with the basic invention earlier described, the platform assembly 12a can be ergonomically conformed to different aspects of the patient's body as needed. The exercise step 14a can be adjusted by the patient to greater or lower elevations relative to the platform 12a and also is provided with a pivotally attached seating service 13a, which can be moved into a seating position to facilitate use of the device with the interchangeable exercycle assembly 15a shown in FIGS. 12, 14A and 14B. The ergonomically adjustable platform 12a with adjustable forearm rests 16a and adjustable handgrips 18a is configured to permit forward and rearward adjustment of the handgrips 18a as well as rotation of the handgrips 18a.

Also included in the alternative embodiment shown in FIGS. 12-16 is the biofeedback assembly, generally shown at 20, as described above. This biofeedback assembly can be adapted to work with each of the interchangeable attachments for flexion, extension, and continuous fluid motion exercise therapy.

The alternative embodiment of the platform assembly 12a can be slightly modified from the earlier described platform assembly 12 shown in FIGS. 1, 2, 3, 4, 5A and 10A to permit entry into the platform assembly by a user from either side. As in the basic platform assembly earlier described, the assembly can be entered by a user from the back side. This direction of entry into the platform is necessary when the seating surface 13a is in a folded down position and used as an adjustable step for maximal flexion exercise therapy.

Figure 12:
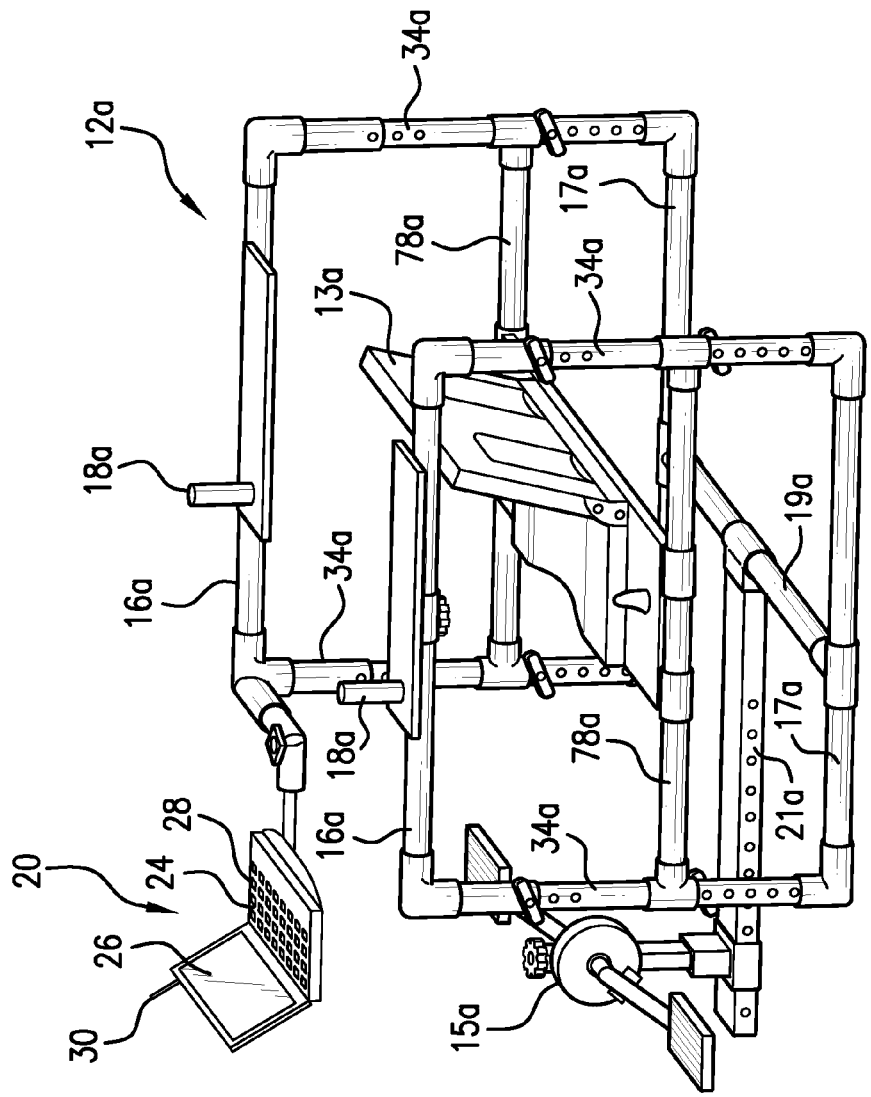
FIG. 12 shows an alternative embodiment of the novel therapy system that includes interchangeable attachments to facilitate maximal flexion, maximal extension, and continuous fluid motion exercise therapy in a single ergonomically adjustable platform.

As shown in FIG. 12, the console connection member 60 shown in the platform assembly 12 for the earlier described embodiment of the invention is eliminated from the modified platform assembly 12a of the more preferred embodiment shown in FIGS. 12-16. Elimination of the connection member 60 is necessary to allow entry by a user into the front end of the platform assembly 12a. Front entry is required to facilitate positioning of the user when working with the interchangeable attachments needed for maximal extension and continuous fluid motion exercise therapy.

The platform assembly 12a can be modified to provide additional structural strength and stability by the addition of side base connectors 17a, which provide laterally disposed connections between the pairs of opposing upright supports 34a. A base connector attachment member 19a, as shown in FIG. 12, can be provided as a structural support connection between the relatively parallel and opposingly disposed side base connectors 17a. The base connection attachment member 19a also provides a detachable securing point for the interchangeable attachment mounting member 21a that can be used to facilitate maximal extension and continuous motion therapy. This attachment mounting member 21a can be configured to permit position adjustment of the interchangeable attachments relative to the platform 12a. This adjustable feature allows the user to properly position the interchangeable attachments to provide the best ergonomic fit to each user.

Figure 13B:
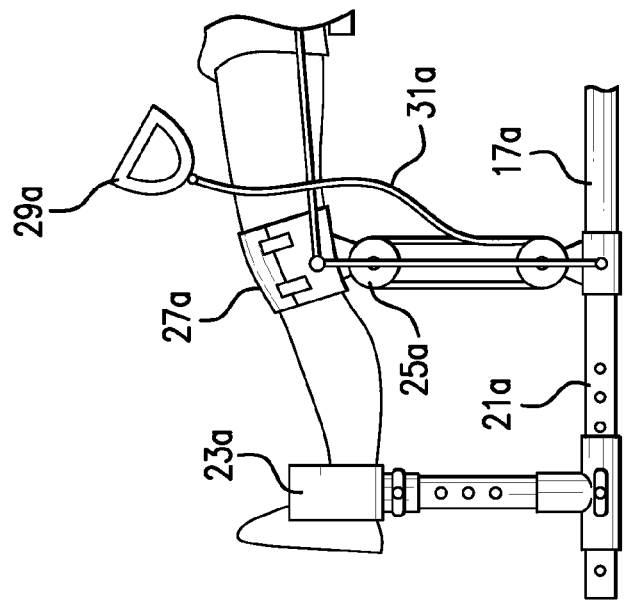
FIG. 13B a detail of ankle yoke, fabric sleeve for the knee, and the double pulley system with an attached griping handle for the embodiment of the therapy system of FIG. 13A.
Figure 13A:
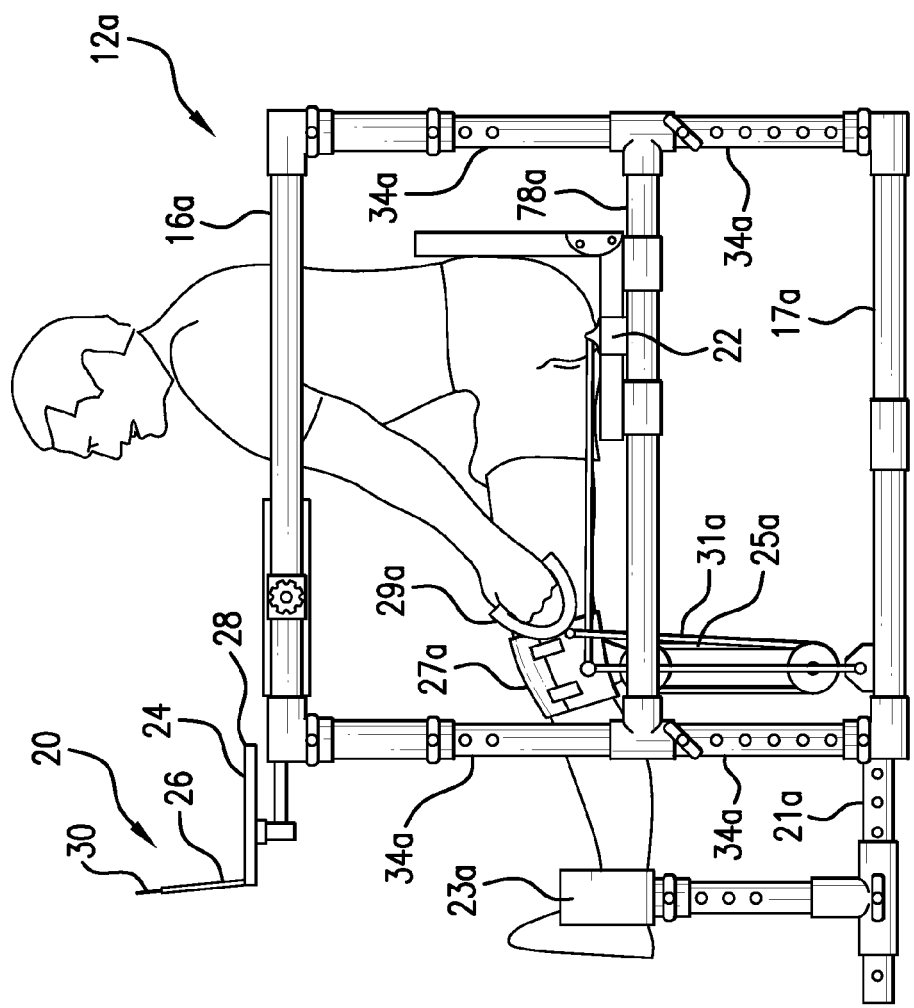
FIG. 13A shows the embodiment of the therapy system of FIG. 12 with the interchangeable attachment for maximal extension.
Figure 14B:
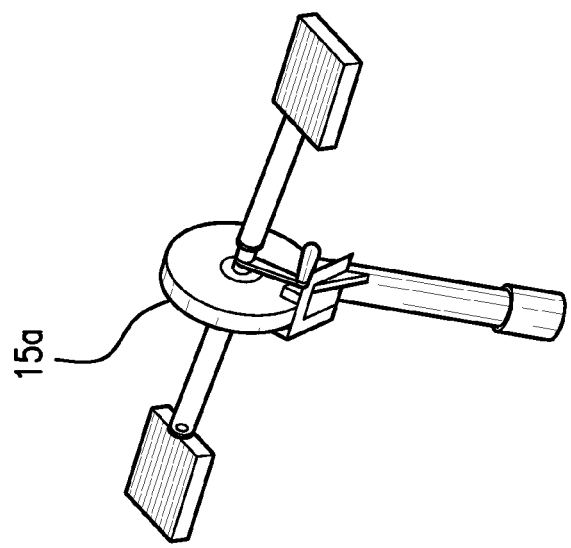
FIG. 14B shows a detail of the interchangeable exercycle attachment for the embodiment of the therapy system of FIG. 14A.
Figure 14A:
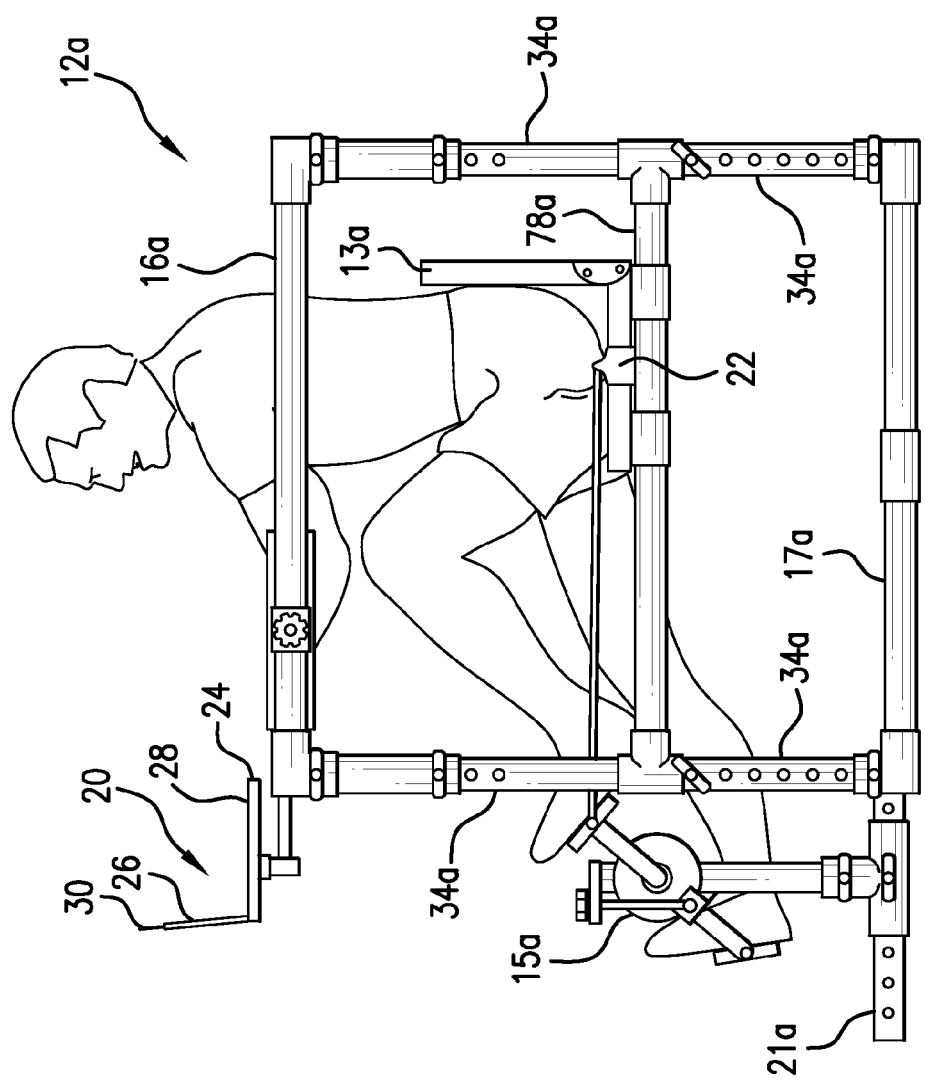
FIG. 14A shows the embodiment of the therapy system of FIG. 12 with the interchangeable attachment for continuous fluid motion.
Figure 15:
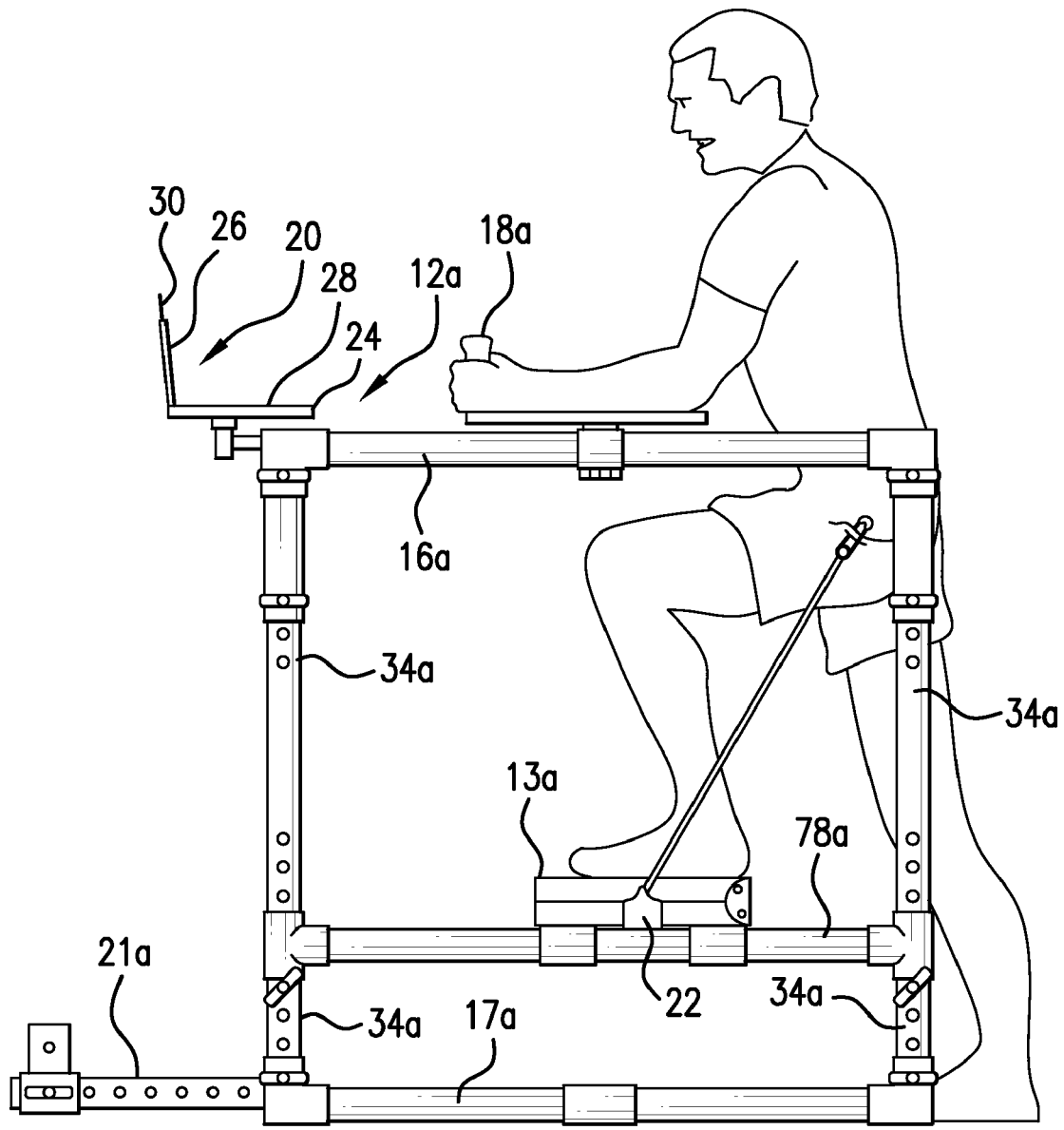
FIG. 15 shows the alternative embodiment of the therapy system of FIG. 12 with the seat folded into a step position for use in maximal flexion exercise therapy.
Figure 16:
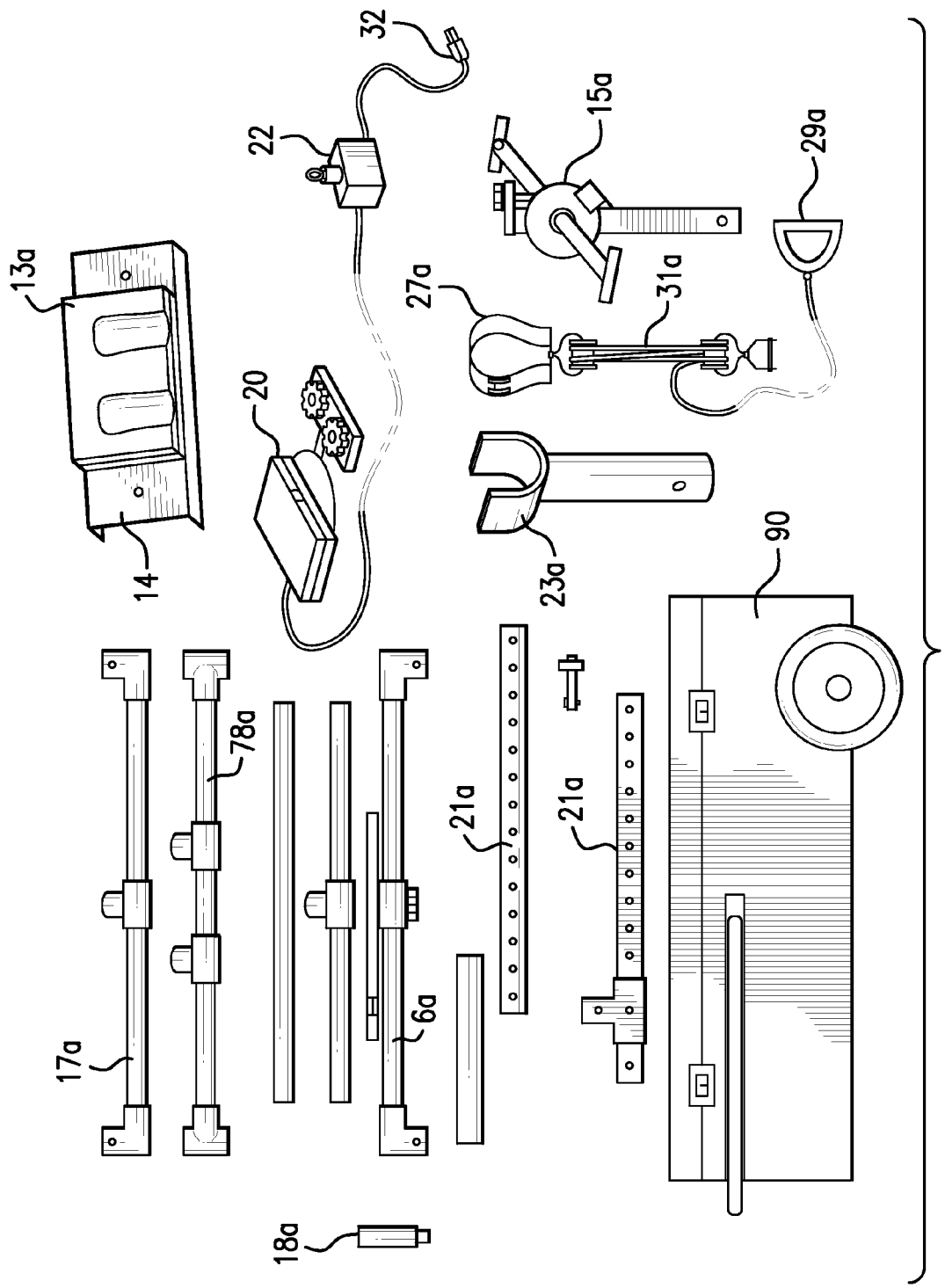
FIG. 16 shows some representative components of the alternative embodiment of the therapy system of FIG. 12 and an alternative wheeled transport container for the same that can be provided as part of a kit. The device so provided can be easily assembled and disassembled for return shipment in the container to the provider.

The more preferred embodiment of the invention shown in FIGS. 12-16 can be provided with interchangeable attachments such as, for example, the exercycle assembly 15a, as shown in FIGS. 12, 14A, 14B and 16, or the ankle yoke and double pulley assembly, as shown in FIGS. 13A, 13B and 16. Each of these interchangeable attachments can be positioned as needed along the length of the attachment mounting member 21a.

The exercycle assembly 15a can be provided as any of a variety of exercise cycle devices known in the art; however, preferable, the exercycle assembly 15a is commercially available disc brake caliper on a custom aluminum disc, mounted on a small, light weight, heavy duty assembly mounted on a standard type lightweight bicycle hub and crank system. Preferably the resistance is smooth and finely adjustable. Resistance adjustment can be accomplished by any method known in the art but preferably can be adjusted using an easily accessible manual device such as a knurled knob located within easy reach at the top of the exercise assembly 15a. Alternatively, the exercise cycle assembly can be provided with any other variable friction device known in the art to permit adjustment of exercise device resistance.

The ankle yoke 23a and double pulley assembly 25a, as shown in FIGS. 13A, 13B and 16, can be adjustably attached to the base connector attachment member 19a to facilitate maximal extension exercise therapy. In operation, the ankle yoke 23a is configured to securely hold the ankle of a subject and a fabric sleeve 27a is placed over the subject's knee and attached to a double pulley assembly 25a. This attachment multiplies the force of the patient pulling lightly on the handle 29a and rope 31a of the double pulley assembly 25a. The subject's control of the double pulley assembly 25a allows force fine tuned by the subject's tolerance for pain and also allows the subject to achieve the large amount of force necessary to overcome the average flexion contracture commonly observed after surgery.

This preferred embodiment of the invention, described above and shown in FIGS. 12-16 allows the subject to challenge himself with three separate but equally important physical therapy assignments: 1) maximal flexion using the adjustable step as described in the basic invention description and shown in FIGS. 1-11; 2) maximal extension using the ankle yoke 23a and double pulley assembly 25a attachment; and 3) continuous fluid motion using the exercycle 15a attachment that can be adjusted to provide increasing resistance to build strength and adjusted to increase the range of fluid flexion achieved.

As shown in FIG. 16, this more preferred multi-function exercise assembly can be provided as an easily assembled device that can be broken down when no longer needed, placed in a container, and shipped back to the provider.

In addition to the embodiment of the multi-function embodiment described and shown in FIGS. 12-16, the platform assembly 12a can be provided as a partial or complete uni-body component construction platform assembly similar to that described for the basic invention platform and shown in FIG. 8. Structural adjustments to such a uni-body component can be made as necessary to facilitate use of the device as described directly above. Similarly, any servo-assisted adjustments to the ergonomic configuration of the device can also be provided in the same manner as earlier described for the basic invention.

Each of the embodiments described above are provided for illustrative purposes only and it is within the concept of the present invention to include modifications and varying configurations without departing from the scope of the invention that is limited only by the claims included herewith.

What is claimed is:

1. An exercise therapy system comprising:
    a platform assembly, said platform assembly comprising:
        at least one elongated upright support, said upright support having a longitudinal axis and an upper end, a middle portion and a lower end, said lower end being configured for stable contact with a supporting surface;
        an adjustable step with a seating surface, said step being adjustably connected to said at least one upright support and being selectively adjustable upward or downward along said longitudinal axis of said at least one upright support, said adjustable step being capable of being locked into a selected position on said at least one might support wherein said adjustable step when so locked provides a stationary step upon which a user of said therapy system can during use position one foot;

a left armrest and a right armrest, each of said left and right armrests being connected to said upper end of said at least one upright support;

a biofeedback assembly connected to said platform assembly, said biofeedback assembly comprising a reference point attachable to a selected position on the body of a user of said therapy system, a measuring mechanism capable of determining each progressive or regressive angular degree of motion of a limb or associated joint during use of said therapy system by measuring the changing distance between said reference point and said stationary step and a computing device capable of converting said measurements into angular measurements.

2. The system of claim 1, wherein said step is provided with a pivotally attached seating surface.

3. The system of claim 1, said platform assembly is connected to a base connector attachment member, said base connector attachment member be configured for adjustable attachment to interchangeable attachments capable of facilitating exercise therapy of a subject.

4. The system of claim 1, further comprising an interchangeable attachment, said interchangeable attachment being selected from the group consisting of an exercycle and an ankle yoke and double pulley assembly.

5. The system of claim 4, wherein said interchangeable attachment is an exercycle, said exercycle being operationally connected to said biofeedback assembly.

6. The system of claim 4, wherein said interchangeable attachment is an ankle yoke and double pulley assembly, said double pulley assembly being operationally connect to said biofeedback system.

7. The system of claim 1, wherein said left and right arm rests are each provided with slidable and pivotally attached hand grips.

8. The system of claim 1, wherein said biofeedback assembly is releasable connected to said exercise platform.

* * * * *